(12) United States Patent
Miyamichi

(10) Patent No.: US 10,136,976 B2
(45) Date of Patent: Nov. 27, 2018

(54) TOOTHBRUSH VIBRATOR

(71) Applicant: M-SYSTEM CO., LTD., Abeno-ku, Osaka-shi, Osaka (JP)

(72) Inventor: Saburo Miyamichi, Osaka (JP)

(73) Assignee: M-SYSTEM CO., LTD., Osaka (JP)

( * ) Notice: Subject to any disclaimer, the term of this patent is extended or adjusted under 35 U.S.C. 154(b) by 0 days.

(21) Appl. No.: 15/543,570

(22) PCT Filed: Jun. 3, 2016

(86) PCT No.: PCT/JP2016/066661
§ 371 (c)(1),
(2) Date: Jul. 13, 2017

(87) PCT Pub. No.: WO2017/208457
PCT Pub. Date: Dec. 7, 2017

(65) Prior Publication Data
US 2018/0214256 A1    Aug. 2, 2018

(51) Int. Cl.
*A46B 13/02*    (2006.01)
*A61C 17/22*    (2006.01)
*A61C 17/34*    (2006.01)

(52) U.S. Cl.
CPC .......... *A61C 17/221* (2013.01); *A46B 13/023* (2013.01); *A61C 17/222* (2013.01); *A61C 17/3481* (2013.01); *A61C 2204/002* (2013.01)

(58) Field of Classification Search
CPC .. A46B 13/023; A61C 17/222; A61C 17/3481
See application file for complete search history.

(56) References Cited

U.S. PATENT DOCUMENTS

| 2,875,458 | A |   | 3/1959  | Tsuda    |              |
|-----------|---|---|---------|----------|--------------|
| 5,283,921 | A | * | 2/1994  | Ng       | A61C 17/22   |
|           |   |   |         |          | 15/145       |
| 5,689,850 | A | * | 11/1997 | Shekalim | A46B 13/02   |
|           |   |   |         |          | 15/145       |
| 6,140,723 | A | * | 10/2000 | Matsui   | A61C 17/3481 |
|           |   |   |         |          | 15/22.1      |

FOREIGN PATENT DOCUMENTS

| CN | 204133632 U  | 2/2015  |
| CN | 205163294 U  | 4/2016  |
| EP | 1652493 A1   | 5/2006  |
| EP | 2550940 A2   | 1/2013  |
| JP | S57-166108 A | 10/1982 |
| JP | S60133931 U  | 9/1985  |
| JP | H102174804 A | 7/1990  |
| JP | H03261407 A  | 11/1991 |

(Continued)

OTHER PUBLICATIONS

Notice of Decision to Grant a Patent for Japanese Application No. P2016-540065 dated Nov. 15, 2016, 6pp.

(Continued)

*Primary Examiner* — Randall Chin
(74) *Attorney, Agent, or Firm* — Hauptman Ham, LLP

(57) ABSTRACT

A toothbrush vibrator according to one embodiment includes a vibration applicator holding a toothbrush and applying a vibration to the toothbrush, and a grip detachably connected to the vibration applicator and gripped by a user.

7 Claims, 28 Drawing Sheets

(56) References Cited

FOREIGN PATENT DOCUMENTS

| | | |
|---|---|---|
| JP | 2003260071 | 9/2003 |
| JP | 2004089353 A | 3/2004 |
| JP | 2006122669 A | 5/2006 |
| JP | 2010213908 A | 9/2010 |
| JP | 3170570 U | 9/2011 |
| JP | 2014530707 | 11/2014 |
| KR | 10-2009-0106306 A | 10/2009 |
| KR | 20-2013-0006950 U | 12/2013 |
| WO | 2013061214 A1 | 5/2013 |

OTHER PUBLICATIONS

Notice of Reasons for Rejection for Japanese Application No. P2016-540065 dated Aug. 30, 2016, 9pp.
Extended European Search Report in EP Application No. 16880188.4, dated Jun. 13, 2018. 5pp.

* cited by examiner

TOOTHBRUSH VIBRATOR

RELATED APPLICATIONS

The present application is a National Phase of International Application Number PCT/JP2016/066661 filed Jun. 3, 2016.

TECHNICAL FIELD

The present invention relates to a toothbrush vibrator.

BACKGROUND ART

In the field of electric toothbrushes, an electric toothbrush in Patent Literature 1 is known. The electric toothbrush in Patent Literature 1 includes a toothbrush receiving part capable of receiving a generic toothbrush and vibrating the toothbrush and a driving part tightly attached to the toothbrush receiving part for transmitting vibration produced by driving of a motor to the toothbrush receiving part. The driving part is fixed to a fixing member provided at the upper end portion (the end portion on the toothbrush bristles side in a state in which the toothbrush is received) of the toothbrush receiving part and is provided at the lower end portion of the toothbrush receiving part in parallel with the toothbrush receiving part.

CITATION LIST

Patent Literature

[Patent Literature 1] Japanese Unexamined Patent Publication No. 2006-122669

SUMMARY OF INVENTION

Technical Problem

In the electric toothbrush described in Patent Literature 1, the driving part and the toothbrush receiving part are disposed in parallel and tightly attached to each other. The user who uses the electric toothbrush therefore grips the driving part together with the toothbrush receiving part during use of the electric toothbrush. In this case, since the toothbrush receiving part and the driving part are gripped by the user, the vibration generated by the motor in the driving part attenuates and is not efficiently transmitted to the toothbrush.

The present invention is then aimed to provide a toothbrush vibrator that can efficiently transmit vibration to a toothbrush.

Solution to Problem

A toothbrush vibrator according to the present invention includes a vibration applicator holding a toothbrush and applying vibration to the toothbrush and a grip detachably connected to the vibration applicator and gripped by a user.

In the configuration above, the vibration applicator and the grip are separate parts and detachably connected to each other. Therefore, even when a user holds the grip, the vibration of the vibration applicator tends not to be attenuated by the user's gripping force. As a result, the vibration of the vibration applicator can be efficiently transmitted to the toothbrush.

The vibration applicator may include a first magnet provided at a grip-side end portion of the vibration applicator. The grip may include a second magnet provided at a vibration applicator-side end portion of the grip. The vibration applicator and the grip may be detachably connected by force of the first magnet and the second magnet attracting each other.

In this configuration, the vibration applicator and the grip are connected so as to attract each other by magnetic force of the first magnet and the second magnet. Therefore, the vibration applicator and the grip are easily attached to and detached from each other.

In a state in which the vibration applicator and the grip are connected to each other, the vibration applicator and the grip may be in point contact. In this case, since the vibration applicator easily swings relative to the grip, the vibration of the vibration applicator tends not to be attenuated. Thus, the vibration of the vibration applicator is transmitted to the toothbrush even more efficiently.

The vibration applicator may include a vibration unit generating vibration to be applied to the toothbrush. The grip may include a power supply unit supplying the vibration unit with electric power. The power supply unit may be electrically connected to the vibration unit in a state in which the grip is connected to the vibration applicator.

This configuration ensures that the vibration unit in the vibration applicator is driven by the power supply unit in the grip when the vibration applicator is attached to the grip.

A first terminal portion electrically connected to the vibration unit may be provided at a grip-side end portion of the vibration applicator. A second terminal portion electrically connected to the power supply unit may be provided at a vibration applicator-side end portion of the grip. The first terminal portion and the second terminal portion may be electrically in contact with each other in a state in which the vibration applicator and the grip are connected to each other.

With this configuration, when the vibration applicator is attached to the grip, the vibration unit and the power supply unit may be electrically connected to each other.

One of the vibration applicator and the grip may include a vibration detector. The power supply unit may control a vibration state of the vibration unit in accordance with a detection result from the vibration detector. In this configuration, the user can brush his/her teeth with a vibration state kept within a predetermined range even when applying the toothbrush on the teeth (even when the load varies so as to suppress vibration).

The grip may include an orientation detector. The power supply unit may control a vibration state of the vibration unit in accordance with a detection result from the orientation detector.

With this configuration, the vibration state may be controlled, for example, depending on how the toothbrush is applied on the teeth (orientation) during toothbrushing. The vibration state thus can be changed, for example, depending on a section of the teeth to be brushed.

The vibration unit may be an eccentric weighted motor.

Advantageous Effects of Invention

The present invention can provide a toothbrush vibrator that can efficiently transmit vibration of the vibration applicator to the toothbrush.

DESCRIPTION OF EMBODIMENTS

Figure 1:
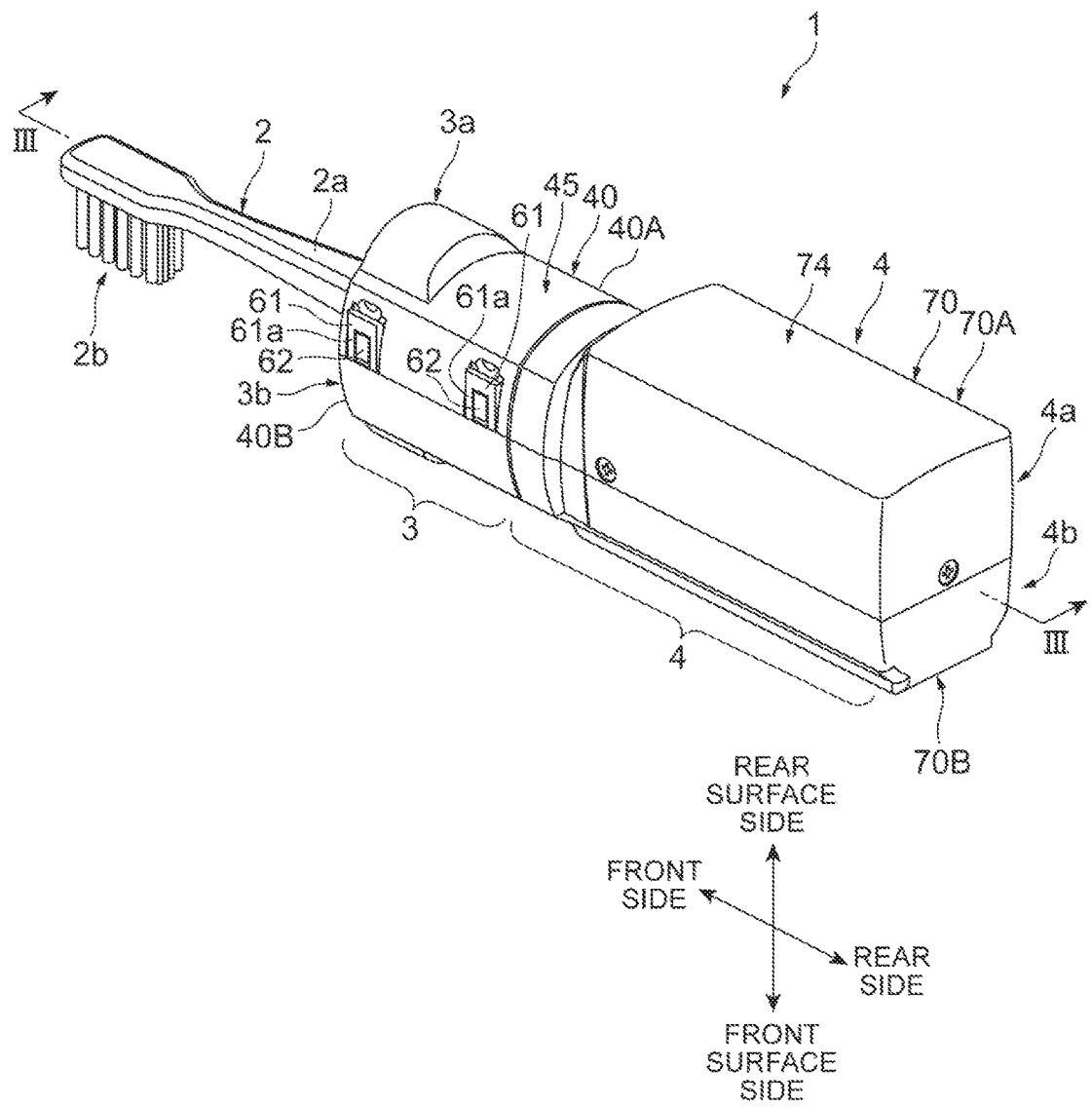
FIG. 1 is a perspective view of a toothbrush vibrator according to an embodiment of the present invention in a state in which a toothbrush is held therein (use state).

Embodiments of the present invention will be described below with reference to the drawings. The same parts are denoted with the same reference signs and an overlapping description will be omitted. The dimensions and shapes in the drawings are not always the same as the actual ones.

Figure 2:
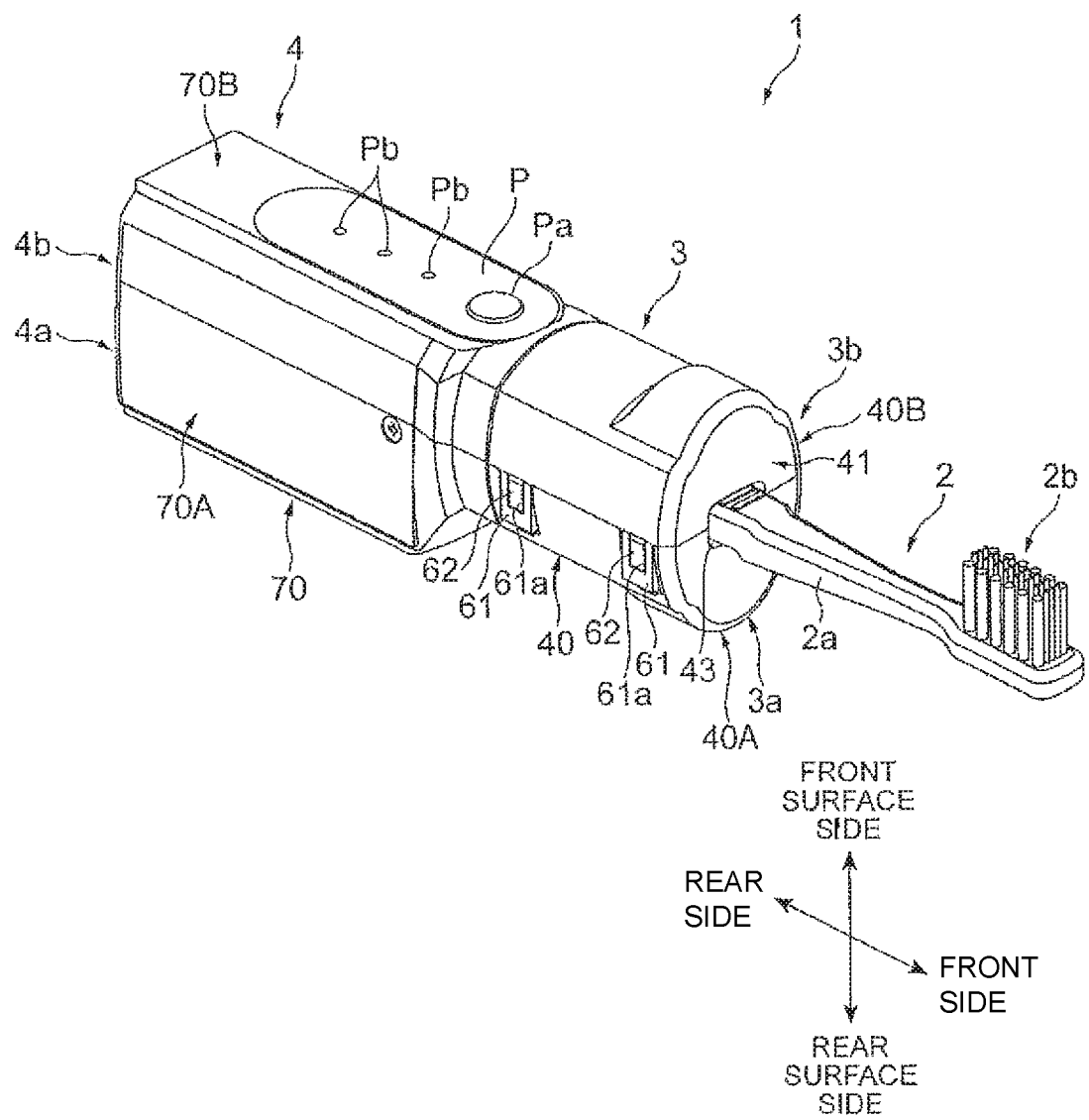
FIG. 2 is a perspective view of the toothbrush vibrator as viewed from the bottom side (the front surface side of the toothbrush) in FIG. 1.
Figure 3:
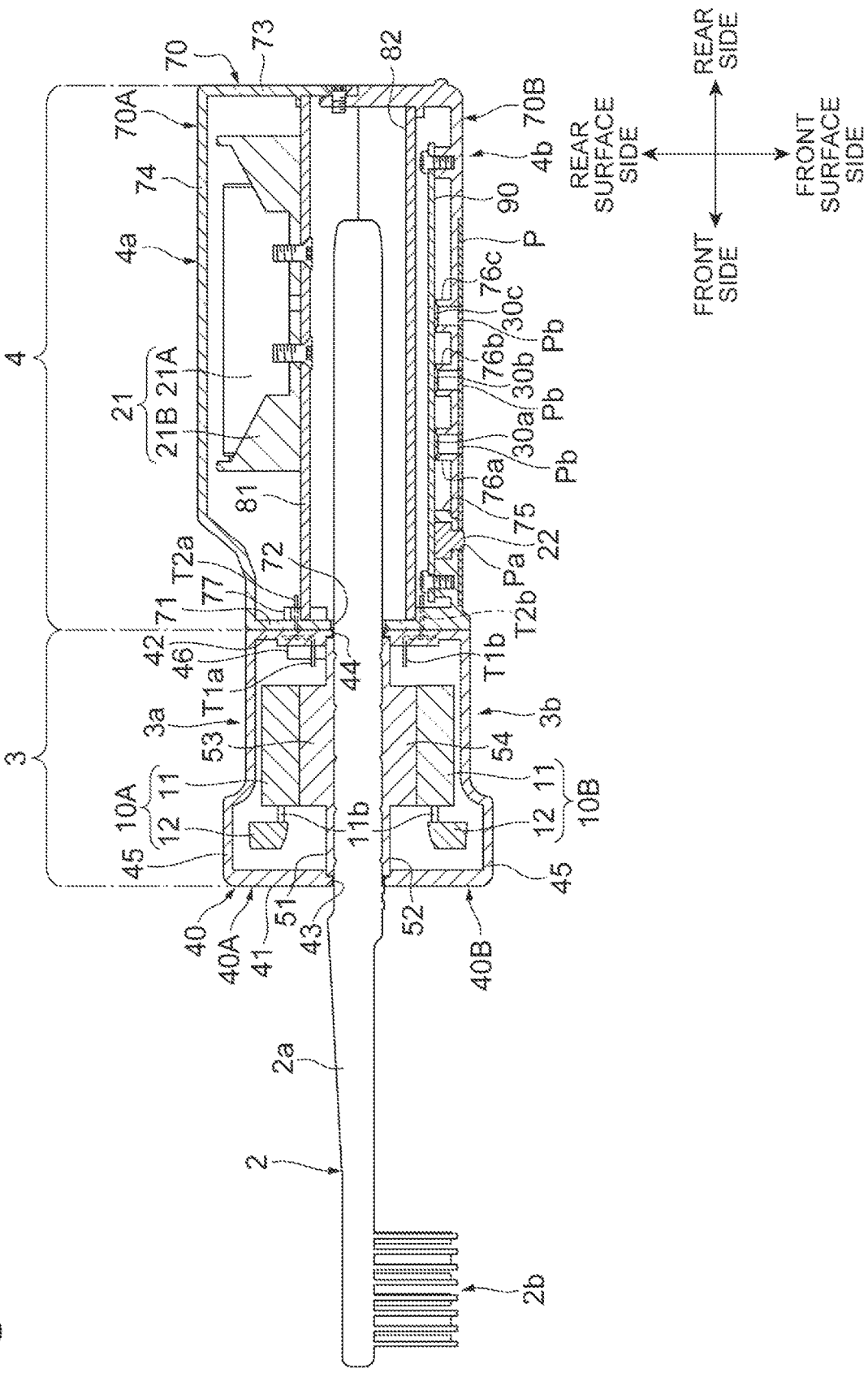
FIG. 3 is a diagram of a cross-sectional configuration along line III-III in FIG. 1.

A toothbrush vibrator (hereinafter simply referred to as "vibrator") 1 schematically shown in FIG. 1 to FIG. 3 is a device that applies vibration to a toothbrush 2 to allow the toothbrush 2 to function as an electric toothbrush. FIG. 1 to FIG. 3 schematically show the use state of the vibrator 1, that is, the state in which the toothbrush 2 is mounted (housed) in the vibrator 1.

In the following, the bristles 2b side in the direction in which the handle 2a of the toothbrush 2 extends will be referred to as the "front side", and the opposite side to the bristles 2b will be referred to as the "rear side", for convenience of explanation. In the thickness direction of the handle 2a of the toothbrush 2 (the length direction of the hairs of the bristles 2b), the side provided with the bristles 2b is referred to as the "front surface side", and the opposite side is referred to as the "rear surface side". Also in the description of the vibrator 1, the aforementioned terms denoting the directions will be used, based on the state in which the toothbrush 2 is attached to the vibrator 1.

The vibrator 1 is a toothbrush holder holding the toothbrush 2. The vibrator 1 is shaped like a pillar extending in the direction in which the handle 2a of the toothbrush 2 extends. The toothbrush 2 held by the vibrator 1 may be a commercially available toothbrush.

The vibrator 1 includes a vibration applicator 3 and a grip 4. The vibration applicator 3 and the grip 4 are separate parts attachable to and detachable from each other. In the present embodiment, the vibration applicator 3 and the grip 4 are detachably coupled to each other using a magnetic force. In the vibrator 1, the vibration applicator 3 is attached to the front end (the bristles 2b side in FIG. 1 to FIG. 3) of the grip 4.

The vibration applicator 3 holds the toothbrush 2 and applies vibration to the toothbrush 2. The grip 4 is a part gripped by the user.

Figure 4:
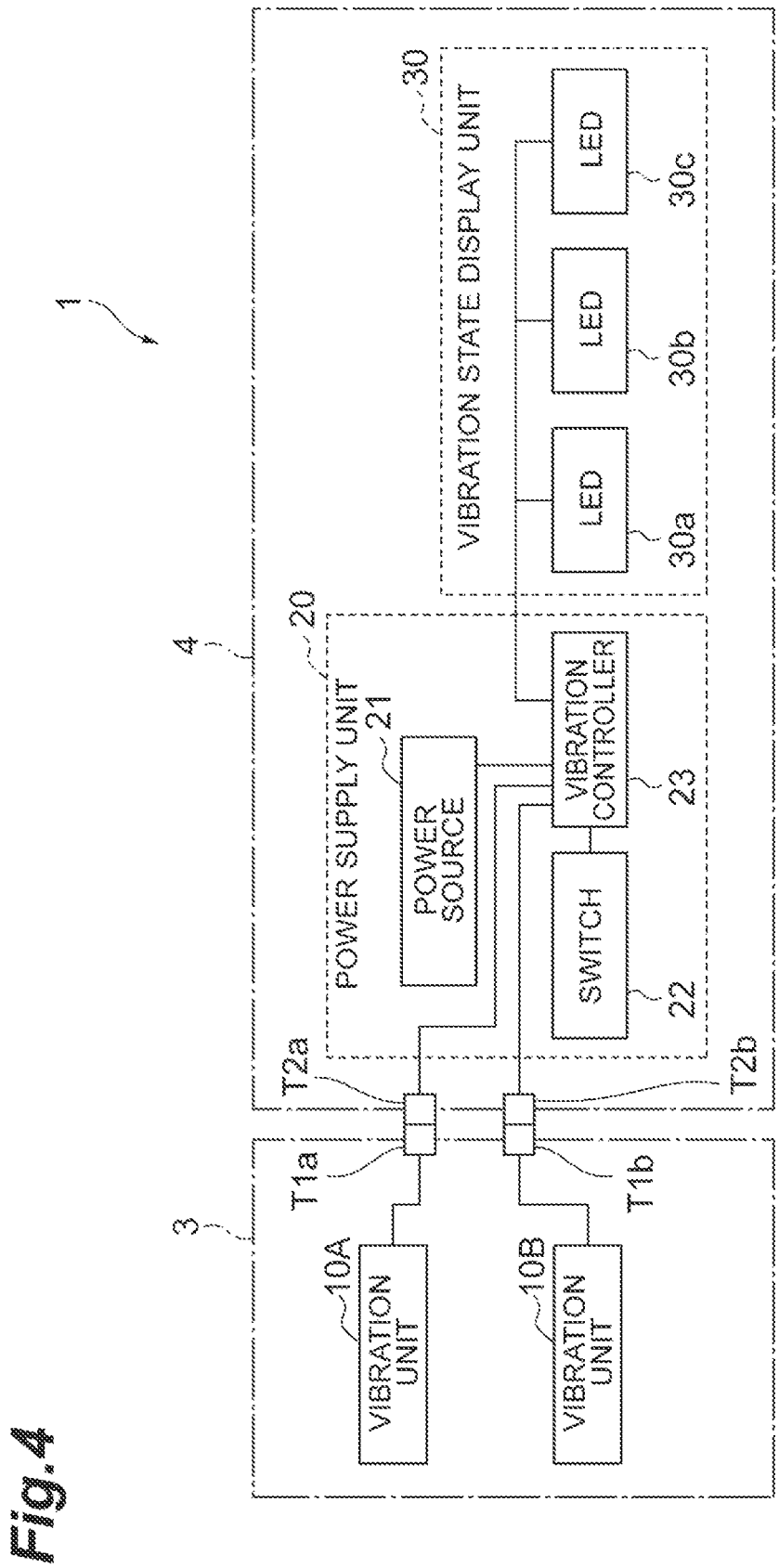
FIG. 4 is a diagram for explaining an electrical connection relation in the toothbrush vibrator.

Referring to FIG. 4, an overview of the vibrator 1 will be described, focusing on the electrical connection in the vibrator 1. FIG. 4 is a block diagram of the vibrator 1 with the vibration applicator 3 attached to the grip 4.

The vibration applicator 3 includes two vibration units 10A and 10B for generating vibration to be applied to the toothbrush 2. The grip 4 includes a power supply unit 20 configured to supply the vibration units 10A and 10B built into the vibration applicator 3 with electric power.

The vibration applicator 3 and the grip 4 include contact terminals (first terminal portion) T1$a$, T1$b$ and contact terminals (second terminal portion) T2$a$, T2$b$, respectively, for electrically connecting the vibration units 10A and 10B to the power supply unit 20 when the vibration applicator 3 is attached to the grip 4. The contact terminal T1$a$ is electrically connected to the vibration unit 10A, and the contact terminal T1$b$ is electrically connected to the vibration unit 10B. The contact terminal T2$a$ is a terminal corresponding to the contact terminal T1$a$ and is electrically connected to the power supply unit 20. The contact terminal T2$b$ is a terminal corresponding to the contact terminal T1$b$ and is electrically connected to the power supply unit 20.

In FIG. 4, the electrical connection is conceptually shown, and the respective one contact terminals T1$a$ and T1$b$ are shown for the vibration units 10A and 10B. However, in order to supply each of the vibration units 10A and 10B with desired electric power, the vibration applicator 3 includes a pair of positive and negative contact terminals T1$a$, T1$a$ for the vibration unit 10A and includes a pair of positive and negative contact terminals T1$b$, T1$b$ for the vibration unit 10B. Thus, the grip 4 also includes the contact terminals T2$a$, T2$a$ corresponding to the contact terminals T1$a$, T1$a$ and includes the contact terminals T2$b$, T2$b$ corresponding to the contact terminals T1$b$, T1$b$.

The power supply unit 20 includes a power source 21, a switch 22, and a vibration controller 23. The power source 21 is a power supply source to supply the vibration units 10A and 10B with electric power and includes, for example, a dry battery. The power source 21 may include a secondary battery instead of a dry battery.

The switch 22 has the function of accepting an instruction to turn on/off the driving of the vibration units 10A and 10B from the user. The switch 22 may include the function of accepting an instruction to switch the vibration state of the vibration units 10A and 10B in multiple levels (low, middle, and high in the present embodiment) in accordance with the user's instruction. In the present embodiment, the switch 22 is a push-button switch and is configured to switch on/off the vibration units 10A and 10B and successively switch the vibration state in the ON state in three levels, namely, low, middle, and high, depending on the number of times the button is pushed. The configuration of the switch 22 is not limited to the push button illustrated above as long as an instruction to switch on/off the vibration units 10A and 10B can be accepted.

The vibration controller 23 is electrically connected to the power source 21, the switch 22, and the contact terminals T2$a$ and T2$b$. The vibration controller 23 controls the vibration state of the vibration units 10A and 10B in accordance with the instruction from the user accepted by the switch 22. Specifically, after the magnitude of electric power supplied from the power source 21 to the vibration units 10A and 10B is adjusted in accordance with the instruction from the user accepted by the switch 22 so that the vibration units 10A and 10B attain the desired vibration state, a predetermined drive signal (predetermined electric power) is supplied to the contact terminals T2$a$ and T2$b$. Since the contact terminals T2$a$ and T2$b$ are electrically connected to the vibration units 10A and 10B through the contact terminals T1$a$ and T1$b$ in a state in which the vibration applicator 3 is attached to the grip 4, the vibration units 10A and 10B can vibrate in the vibration state in accordance with the user's instruction. In the first embodiment, the manner in which the vibration controller 23 drives the vibration units 10A and 10B such that they attain a similar vibration state will be mainly described. However, the vibration controller 23 may drive the vibration units 10A and 10B in different vibration states. That is, the vibration controller 23 may perform control such that one of the vibration unit 10A and the vibration unit 10B is driven and the other is not driven.

The grip 4 may include a vibration state display unit 30 for indicating the vibration state of the vibration units 10A and 10B to the user. In the present embodiment, as schematically shown in FIG. 3, the vibration state display unit 30 includes three LEDs 30$a$, 30$b$, and 30$c$. The LEDs 30$a$, 30$b$, and 30$c$ are each electrically connected to the vibration controller 23. The light emission states of the LEDs 30$a$, 30$b$, and 30$c$ are controlled by the vibration controller 23. For example, when the vibration units 10A and 10B are in the OFF state, all the LEDs 30$a$, 30$b$, and 30$c$ are controlled in a non-light emission state. When the vibration units 10A and 10B are vibrated in each of the low vibration state, the middle vibration state, and the high vibration state, the control is performed such that any of the three LEDs 30$a$, 30$b$, and 30$c$ are in the illumination state in accordance with each vibration state.

Figure 5:
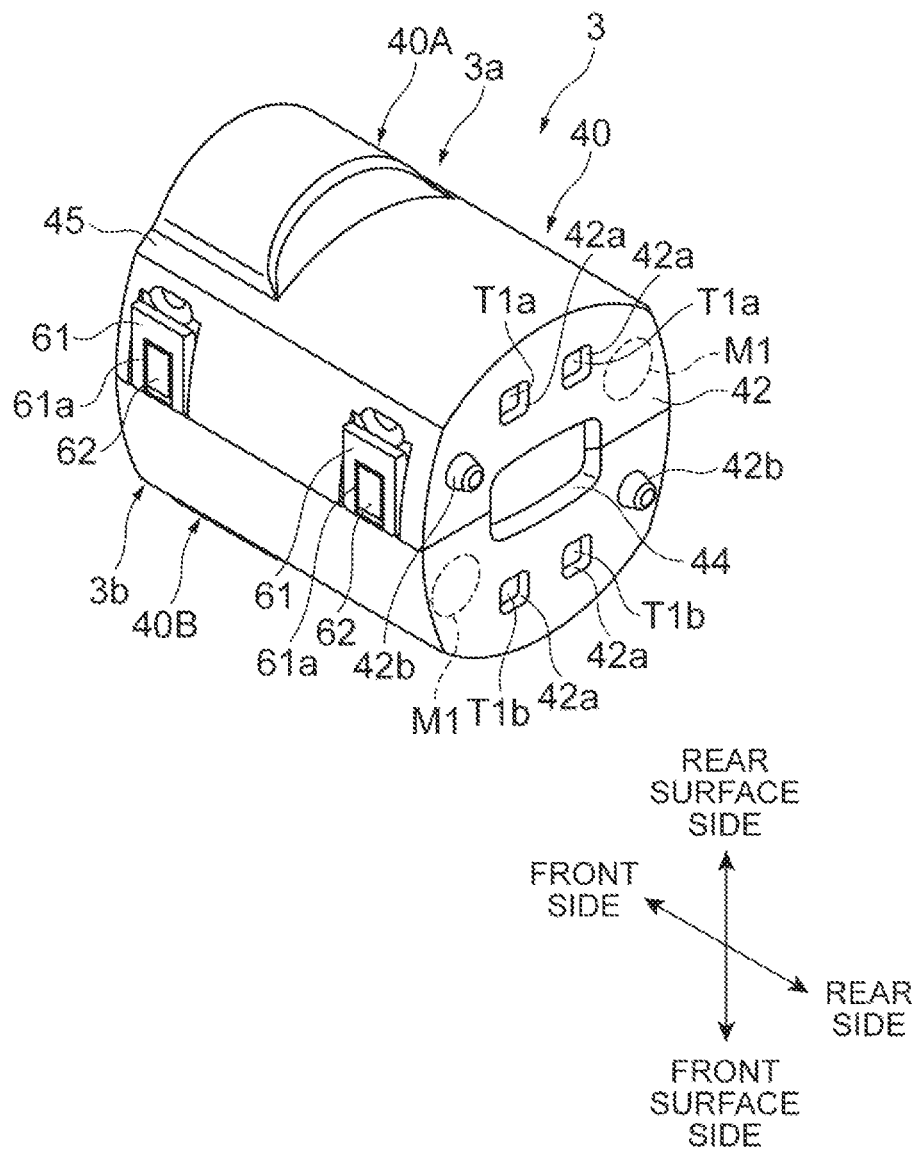
FIG. 5 is a perspective view of the vibration applicator of the toothbrush vibrator shown in FIG. 1.
Figure 6:
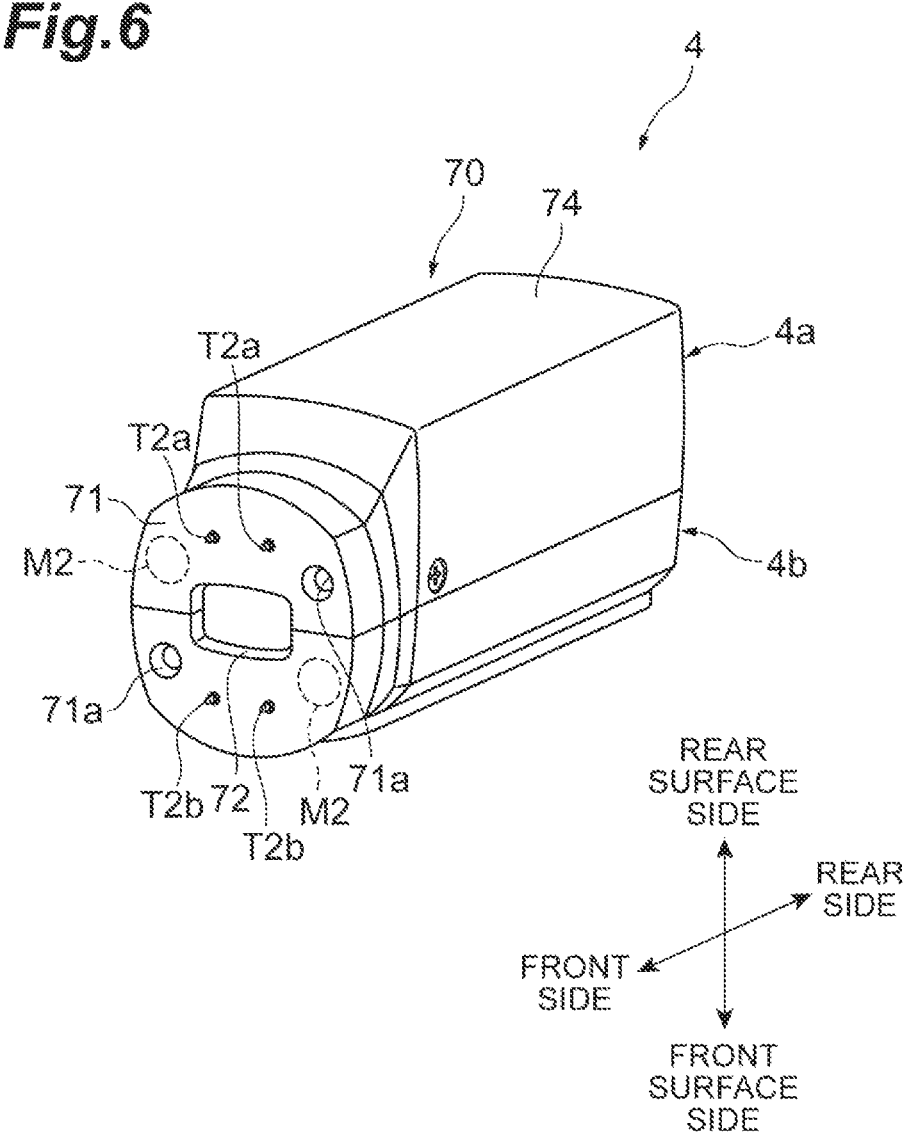
FIG. 6 is a perspective view of the grip of the toothbrush vibrator shown in FIG. 1.

Referring now to FIG. 1 to FIG. 3, FIG. 5, and FIG. 6, an example of the configuration of the vibration applicator 3 and the grip 4 will be described. In FIG. 3, the electrical wiring in the vibrator 1 is not illustrated. FIG. 5 is a perspective view of the vibration applicator 3 as viewed from the grip 4, and FIG. 6 is a perspective view of the grip 4 as viewed from the vibration applicator 3.

<Vibration Applicator>

The vibration applicator 3 includes a case 40, vibration units 10A and 10B, contact terminals T1$a$, T1$a$, T1$b$, and T1$b$, and first magnets M1 and M1.

The case 40 is a hollow pillar-shaped body. A case front wall 41 (see FIG. 2 and FIG. 3) and a case rear wall 42 (see FIG. 3 and FIG. 5) have a first opening 43 and a second opening 44, respectively, to allow the handle 2$a$ of the toothbrush 2 to pass through. The case front wall 41 is a wall positioned on the opposite side to the side on which the grip 4 is connected in the vibration applicator 3. The case rear wall (grip-side end portion) 42 is a wall on the side connected to the grip 4 in the vibration applicator 3. The material of the case 40 is, for example, resin such as polycarbonate (PC) or may be metal rather than resin.

The shape and the size of the first opening 43 and the second opening 44 substantially match the shape and the maximum size of the region of the handle 2$a$ that is inserted into the vibration applicator 3 (hereinafter referred to as "first inserted region"). In the case 40, a pair of partition plates 51 and 52 are fixed to the case 40 so that the handle 2$a$ is interposed therebetween. A pair of partition plates 51 and 52 may be fixed by screwing or may be fixed with adhesive. The material of a pair of partition plates 51 and 52 is, for example, resin such as polycarbonate (PC) or may be metal rather than resin. The distance between a pair of partition plates 51 and 52 is substantially equal to the thickness of the thickest portion of the first inserted region of the handle 2$a$ in the vibration applicator 3. Thus, the first opening 43, the gap between a pair of partition plates 51 and 52, and the second opening 44 form an insertion region for the handle 2$a$. When the shape and the size of the first opening 43 and the second opening 44 as well as the distance between a pair of partition plates 51 and 52 have the relation described above, the handle 2$a$ can be inserted into the case 40 and the toothbrush 2 can be held in the case 40. The distance between a pair of partition plates 51 and 52 may be, for example, longer than the thickness of the thickest portion of the first inserted region of the handle 2a in the vibration applicator 3 as long as the handle 2a can be held in the first opening 43 and the second opening 44.

The vibration unit 10A is an eccentric weighted motor with an eccentric weight 12 eccentrically fixed to the shaft 11b of a motor 11. The vibration unit 10A is housed in a region that is closer to the rear surface than the partition plate 51 and between peripheral wall 45 of the case 40 and the partition plate 51. A support base 53 is fixed to the partition plate 51, and the vibration unit 10A is fixed to the support base 53 such that the eccentric weight 12 is rotatable. Specifically, the motor 11 is fixed to the support base 53 such that the eccentric weight 12 does not abut with the support base 53. The support base 53 may be formed integrally with the partition plate 51. The thickness of the support base 53 may be of a height that allows rotation of the eccentric weight 12. As shown in FIG. 3, the peripheral wall 45 of the case 40 may have a shape that can provide a region in which the eccentric weight 12 rotates.

The vibration unit 10B has the same configuration as the vibration unit 10A. That is, the vibration unit 10B is an eccentric weighted motor with an eccentric weight 12 eccentrically fixed to the shaft 11b of the motor 11. The vibration unit 10B is housed in a region that is closer to the front surface than the partition plate 52 and between the peripheral wall 45 of the case 40 and the partition plate 52. A support base 54 is formed on the partition plate 52, and the vibration unit 10B is fixed to the support base 54 such that the eccentric weight 12 is rotatable. Specifically, the motor 11 is fixed to the support base 54 such that the eccentric weight 12 does not abut with the support base 54. The thickness of the support base 54 may be of a height that allows rotation of the eccentric weight 12.

As shown in FIG. 3 and FIG. 5, the contact terminals T1a and T1b are fixed to the case rear wall (the grip-side end portion of the vibration applicator) 42. The contact terminal T1a is fixed to the rear surface side of the case rear wall 42 (in the manner shown in FIG. 3 and FIG. 5, closer to the rear surface than the second opening 44), and the contact terminal T1b is fixed to the front surface side of the case rear wall 42 (in the manner shown in FIG. 3 and FIG. 5, closer to the front surface than the second opening 44).

As shown in FIG. 3, the contact terminals T1a and T1b are a conductor plate shaped like the letter L. The contact terminals T1a and T1b are partially embedded in the case rear wall 42, and the regions other than the embedded regions of the contact terminals T1a and T1b extend into the case 40 for electrical connection of the vibration unit 10A and the vibration unit 10B with the contact terminals T1a and T1b. In order to supply a predetermined drive signal from the power supply unit 20 to the contact terminals T1a and T1b, as shown in FIG. 5, holes 42a are formed in part of the case rear wall 42 so as to expose the contact terminals T1a and T1b.

As shown in FIG. 5, the first magnet M1 is fixed on the inside of the case rear wall 42. The first magnet M1 is thus provided at a rear end portion (grip-side end portion) of the vibration applicator 3. An example of the first magnet M1 is a permanent magnet. In the present embodiment, the first magnets M1 are disposed on the inside at the lower left portion and the upper right portion of the case rear wall 42 when the vibration applicator 3 is viewed from the grip 4. The first magnet M1 may be shaped like, for example, but not limited to, a disk or a ball. As schematically shown in FIG. 3, the first magnet M1 may be fixed, for example, in a magnet housing 46 provided on the inside of the case rear wall 42. It is noted that the first magnet M1 may be directly fixed to the case rear wall 42. The first magnet M1 may be fixed by any method that prevents the first magnet M1 from moving and, for example, may be fixed with adhesive.

Two first magnets M1 may be disposed such that the same magnetic poles (north pole or south pole) are positioned on the grip 4 side or may be disposed such that the magnetic poles are different from each other, that is, for example, the grip 4-side surface of one of the first magnets M1 is the north pole and the grip 4-side surface of the other first magnet M1 is the south pole.

As shown in FIG. 5, an alignment protrusion 42b may be formed on the case rear wall 42 of the vibration applicator 3 for alignment in attaching the vibration applicator 3 to the grip 4. Although a single alignment protrusion 42b may be formed, it is preferable that two alignment protrusions 42b are formed as shown in FIG. 5 in order to further ensure the alignment between the vibration applicator 3 and the grip 4. In FIG. 5, the alignment protrusions 42b are provided at the upper left and the lower right when the case rear wall 42 is viewed from the grip 4. However, the position of the alignment protrusions 42b is not limited to the manner shown in FIG. 5. Three or more alignment protrusions 42b may be provided.

The vibration applicator 3 is obtained, for example, by producing and then assembling a rear surface-side part 3a and a front surface-side part 3b having a configuration in which the vibration applicator 3 is divided by a virtual plane orthogonal to the thickness direction of the handle 2a and including the axis of the handle 2a in a state in which the toothbrush 2 is held by the vibration applicator 3.

The rear surface-side part 3a may be produced, for example, as follows. First of all, a first case portion 40A is fabricated, which corresponds to the rear surface-side portion of the case 40 divided by the above-noted virtual plane. In doing so, the first case portion 40A is produced in a state in which the contact terminal T1a is partially embedded in the rear wall of the first case portion 40A that forms part of the case rear wall 42. For example, when the case 40 is made of resin, the first case portion 40A can be fabricated by injection molding. Subsequently, the first magnet M1 is fixed to the inside of the rear wall of the first case portion 40A. Concurrently with these operations, the partition plate 51 is prepared, which has the support base 53 to which the vibration unit 10A is fixed. Subsequently, the vibration unit 10A is wired to the contact terminal T1a, and then the partition plate 51 is fixed to the first case portion 40A such that the vibration unit 10A is positioned on the inside of the first case portion 40A. The rear surface-side part 3a is thus obtained.

The front surface-side part 3b may be produced in the same manner as the rear surface-side part 3a, except that the contact terminal T1b is employed instead of the contact terminal T1a so as to fabricate a second case portion 40B to be paired with the first case portion 40A, and the vibration unit 10B is employed instead of the vibration unit 10A.

The vibration applicator 3 may be produced by assembling the rear surface-side part 3a and the front surface-side part 3b obtained as described above, for example, by screwing or engagement.

In the manner shown in FIG. 1, FIG. 2, and FIG. 5, the front surface-side part 3b has a plate portion 61 erected toward the rear surface-side part 3a, and a pawl 62 is formed on the outer surface of the rear surface-side part 3a. The pawl 62 of the rear surface-side part 3a is then engaged with a hole 61a formed in the plate portion 61 of the front surface-side part 3b to construct the vibration applicator 3.

In the configuration of the vibration applicator 3 above, the vibration units 10A and 10B are fixed to the support bases 53 and 54 on the partition plates 51 and 52, and the partition plates 51 and 52 are fixed to the case 40. Thus, when the vibration units 10A and 10B vibrate, the vibration applicator 3 vibrates, and this vibration is transmitted to the toothbrush 2 held in the case 40.

The vibration applicator 3 is internally provided with the vibration units 10A and 10B, which are eccentric weighted motors, and has any configuration as long as it can hold the toothbrush 2 so as to transmit the vibration of the vibration units 10A and 10B to the toothbrush 2 and is attachable to and detachable from the grip 4.

<Grip>

The grip 4 includes a case 70, contact terminals T2a, T2a, T2b, and T2b, and second magnets M2 and M2.

The case 70 is a hollow pillar-shaped body. A case front wall (the vibration applicator-side end portion of the grip) 71 has an opening 72 to allow the handle 2a of the toothbrush 2 to pass through. The case front wall 71 is a wall positioned on the vibration applicator 3 side in the grip 4. The shape and the size of the opening 72 substantially match the shape and the size of the front end of the region of the handle 2a that is inserted into the grip 4 (hereinafter referred to as "second inserted region"). In the present embodiment, a case rear wall 73 has no opening. The material of the case 70 is, for example, resin such as polycarbonate (PC) or may be metal rather than resin.

A pair of partition plates 81 and 82 are fixed to the case 70 so that the handle 2a is interposed therebetween. A pair of partition plates 81 and 82 may be fastened by screws to the case 70 or may be fixed with adhesive. The material of a pair of partition plates 81 and 82 is, for example, resin such as polycarbonate (PC) or may be metal rather than resin. The distance between a pair of partition plates 81 and 82 is equal to or greater than the thickness of the second inserted region of the handle 2a in the grip 4 and, for example, there may be a gap between the partition plate 81 and the handle 2a and between the partition plate 82 and the handle 2a, as shown in FIG. 3.

In the configuration above, when the vibration applicator 3 is attached to the grip 4, the portion of the handle 2a of the toothbrush 2 that protrudes from the case rear wall 42 of the vibration applicator 3 can be housed in the grip 4.

The power source 21 is housed in a region that is closer to the rear surface than the partition plate 81 and between a peripheral wall 74 of the case 70 and the partition plate 81. In the manner shown in FIG. 3, the power source 21 includes a dry battery 21A. The dry battery 21A is housed in a battery box 21B fixed to the partition plate 81. FIG. 3 illustrates a manner in which the battery box 21B is fastened by screws to the partition plate 81. As long as the battery box 21B is fixed to the partition plate 81, the method of fixing is not limited to screwing. The battery box 21B may be fixed to the partition plate 81, for example, with adhesive.

A circuit board 90 is housed in a region that is closer to the front surface than the partition plate 82 and between the peripheral wall 74 of the case 70 and the partition plate 82. As shown in FIG. 3, the circuit board 90 may be fixed to the case 70 by screwing or may be fixed with adhesive.

The switch 22 and three LEDs 30a, 30b, and 30c are mounted on the circuit board 90. The circuit board 90 includes a circuit corresponding to the vibration controller 23 shown in FIG. 4. The electrical connection relation between the switch 22, the vibration controller 23, and the LEDs 30a, 30b, and 30c has been described with reference to FIG. 4 and will not be further elaborated here. Their electrical connection may be implemented by wiring on the circuit board 90. As illustrated with FIG. 4, the power source 21 is electrically connected with the vibration controller 23. This may be implemented by installing wiring from the battery box 21B to the circuit board 90. In order to install wiring from the battery box 21B to the circuit board 90, for example, a hole or a notch for wiring may be formed in the partition plates 81 and 82.

In the manner shown in FIG. 3, tubular portions 75, 76a, 76b, and 76c corresponding to the switch 22 and the LEDs 30a, 30b, and 30c, respectively, are erected on the inside of a region on the front surface side of the peripheral wall 74 of the case 70, that is, a region opposed to the partition plate 82.

The switch 22 is housed in the tubular portion 75, and the tip end portion of the switch 22 is exposed on the outside of the case 70 through the opening in the tubular portion 75. This allows the user to push the switch 22.

The LEDs 30a, 30b, and 30c are surrounded with the corresponding tubular portions 76a, 76b, and 76c. This enables light from the LEDs 30a, 30b, and 30c to be efficiently output to the outside through the openings in the tubular portion 76a, 76b, 76c without diffusing.

As shown in FIG. 2 and FIG. 3, in an embodiment, a nameplate film P may be affixed to the front surface side of the peripheral wall 74. When the nameplate film P covers the openings in the tubular portions 75, 76a, 76b, and 76c formed in the peripheral wall 74 of the case 70, an opening Pa is formed in the nameplate film P so as to expose the tip end portion of the switch 22, and, in addition, translucent windows Pb, Pb, and Pb are formed corresponding to the LEDs 30a, 30b, and 30c such that light from the LEDs 30a, 30b, and 30c can be output.

As shown in FIG. 3 and FIG. 6, the contact terminals T2a and T2b are fixed to the case front wall 71. The contact terminals T2a and T2b are fixed to the positions corresponding to the contact terminals T1a and T1b shown in FIG. 5, more specifically the positions corresponding to the holes 42a in the case rear wall 42 shown in FIG. 5. The contact terminals T2a and T2b are rod-shaped spring connectors and are fixed to the case front wall 71 so as to pass through the case front wall 71.

Since the contact terminals T2a and T2b are fixed at the positions corresponding to the holes 42a in the case rear wall 42 shown in FIG. 5, the contact terminal T2a and the contact terminal T2b come into contact with the corresponding contact terminal T1a and contact terminal T1b, respectively, when the vibration applicator 3 is attached to the grip 4. Furthermore, since the contact terminals T2a and T2b are spring connectors, the contact of the contact terminal T2a and the contact terminal T2b with the contact terminal T1a and the contact terminal T1b can be kept even when the vibration applicator 3 vibrates. As a result, a signal from the power supply unit 20 (more specifically, the vibration controller 23) to the vibration units 10A and 10B can be stably supplied.

As shown in FIG. 6, the second magnet M2 is fixed on the inside of the case front wall 71. Thus, the second magnet M2 is provided at the front-end portion (the vibration applicator-side end portion) of the grip 4. An example of the second magnet M2 is a permanent magnet. In the present embodiment, the second magnet M2 may be provided at a position corresponding to the first magnet M1. In the present embodiment, given that the first magnets M1 are provided at the lower left portion and the upper right portion of the case rear wall 42 when the vibration applicator 3 is viewed from the grip 4, as shown in FIG. 5, the second magnets M2 are disposed at the upper left portion and the lower right portion of the case front wall 71 when the grip 4 is viewed from the vibration applicator 3, as shown in FIG. 6. The second magnet M2 may be shaped like, for example, but not limited to, a disk or a ball. As schematically shown in FIG. 3, for example, the second magnet M2 may be fixed in a magnet housing 77 provided on the inside of the case front wall 71. The second magnet M2 may be fixed by any method that prevents the second magnet M2 from moving and, for example, may be fixed with adhesive.

Each of the second magnets M2 is disposed and fixed such that the opposite magnetic pole to that of the grip 4-side surface of the corresponding first magnet M1 is positioned on the vibration applicator 3 side. This allows the vibration applicator 3 to be detachably attached to the grip 4 by magnetic force of the first magnets M1 and the second magnets M2.

When the case rear wall 42 of the vibration applicator 3 has the alignment protrusions 42b as shown in FIG. 5, the case front wall 71 has depressions 71a corresponding to the alignment protrusions 42b to receive the alignment protrusions 42b. In this case, the vibrator 1 may be constructed by fitting the alignment protrusions 42b in the depressions 71a to easily align the vibration applicator 3 with the grip 4.

The grip 4 can be obtained, for example, by producing and then assembling a rear surface-side part 4a and a front surface-side part 4b having a configuration in which the grip 4 is divided by a virtual plane orthogonal to the thickness direction of the handle 2a and including the axis of the handle 2a in a state in which the handle 2a of the toothbrush 2 is inserted in the grip 4.

The rear surface-side part 4a may be produced, for example, as follows. First of all, a first case portion 70A is produced, which corresponds to the rear surface-side portion of the case 70 divided by the virtual plane. In doing so, the first case portion 70A is produced in a state in which the contact terminal T2a is partially embedded in the front wall of the first case portion 70A that forms part of the case front wall 71. For example, when the case 70 is made of resin, the first case portion 70A can be fabricated by injection molding. Subsequently, the second magnet M2 is fixed to the inside of the front wall of the first case portion 70A. Concurrently with these operations, the partition plate 81 to which the power source 21 is fixed is prepared. Subsequently, the partition plate 81 is fixed to the first case portion 70A such that the power source 21 is positioned on the inside of the first case portion 70A. The rear surface-side part 4a is thus obtained. Wire lines such as conductors may extend to the outside to allow for wiring between the circuit board 90 and the power source 21, at a stage before the partition plate 81 is fixed to the first case portion 70A.

Similarly, the front surface-side part 4b may be produced, for example, as follows. First of all, a second case portion 70B is fabricated, which corresponds to the front surface-side portion of the case 70 divided by the virtual plane. In doing so, the second case portion 70B is fabricated in a state in which the contact terminal T2b is partially embedded in the front wall of the second case portion 70B that forms part of the case front wall 71. For example, when the case 70 is made of resin, the second case portion 70B can be fabricated by injection molding. Subsequently, the second magnet M2 is fixed to the inside of the front wall of the second case portion 70B. Concurrently with these operations, the circuit board 90 mounted with the switch 22, the vibration controller 23, and the LEDs 30a, 30b, and 30c is wired with the power source 21, and the circuit board 90 is then fixed to the second case portion 70B. Subsequently, the partition plate 82 is fixed to the second case portion 70B. The front surface-side part 4b is thus obtained.

The grip 4 may be produced by assembling the rear surface-side part 4a and the front surface-side part 4b produced as described above, for example, by screwing or engagement.

When the user brushes his/her teeth using the vibrator 1 described above, first, the user inserts the handle 2a of the toothbrush 2 through the vibration applicator 3 to hold the toothbrush 2 in the vibration applicator 3. Subsequently, the vibration applicator 3 is attached to the grip 4 by magnetic force of the first magnets M1 and the second magnets M2 to assemble the vibrator 1. In doing so, in the manner in which the alignment protrusions 42b are provided, the alignment protrusions 42b are fitted in the depressions 71a for receiving the protrusions to facilitate attachment of the vibration applicator 3 to the grip 4 at a predetermined position.

Subsequently, the user pushes the switch 22, which is a push button switch, to vibrate the vibration units 10A and 10B with a desired intensity and brushes his/her teeth while vibrating the toothbrush 2.

In the vibrator 1, the vibration applicator 3 and the grip 4 are separate parts and configured to be attachable to and detachable from each other. Thus, even when the user holds the grip 4, the vibration of the vibration applicator 3 tends not to be attenuated by the user's gripping force. As a result, the vibration of the vibration applicator 3 can be efficiently transmitted to the toothbrush 2. Furthermore, a plurality of vibration applicators 3 each adapted to the size of the handle 2a of the toothbrush 2 may be prepared so that toothbrushes with different sizes can be used as an electric toothbrush simply by changing the vibration applicators 3 for the same grip 4.

Since the vibration applicator 3 and the grip 4 are coupled by the magnetic force of the first magnets M1 and the second magnets M2, the vibration applicator 3 and the grip 4 can be easily attached to and detached from each other. Because of the magnetic coupling, the vibration applicator 3 easily swings even when the grip 4 is gripped. This further facilitates transmission of the vibration of the vibration applicator 3 to the toothbrush 2.

Moreover, since the power supply unit 20, that is, the power source 21, the vibration controller 23, and the like are housed in the grip 4, the weight of the vibration applicator 3 is reduced. This facilitates vibration of the vibration applicator 3 and can increase the intensity of vibration transmitted to the toothbrush 2.

Since the vibration applicator 3 includes two vibration units 10A and 10B, the vibration intensity of the vibration applicator 3 is high. As a result, the vibration intensity of the toothbrush 2 is also high to enable efficient toothbrushing. Moreover, the provision of two vibration units 10A and 10B increases the degree of freedom in adjustment of the vibration intensity of the vibration applicator 3. This expands the range of adjustment and allows the user to brush his/her teeth with a preferred intensity. It is noted that the vibration applicator 3 includes at least one vibration unit.

Referring now to the experiment results, the operations and effects of the vibrator 1 will be described specifically. In the description of the experiment results, the elements corresponding to the components of the vibrator 1 will be denoted with the same reference signs.

[Experimental Device]

Figure 7:
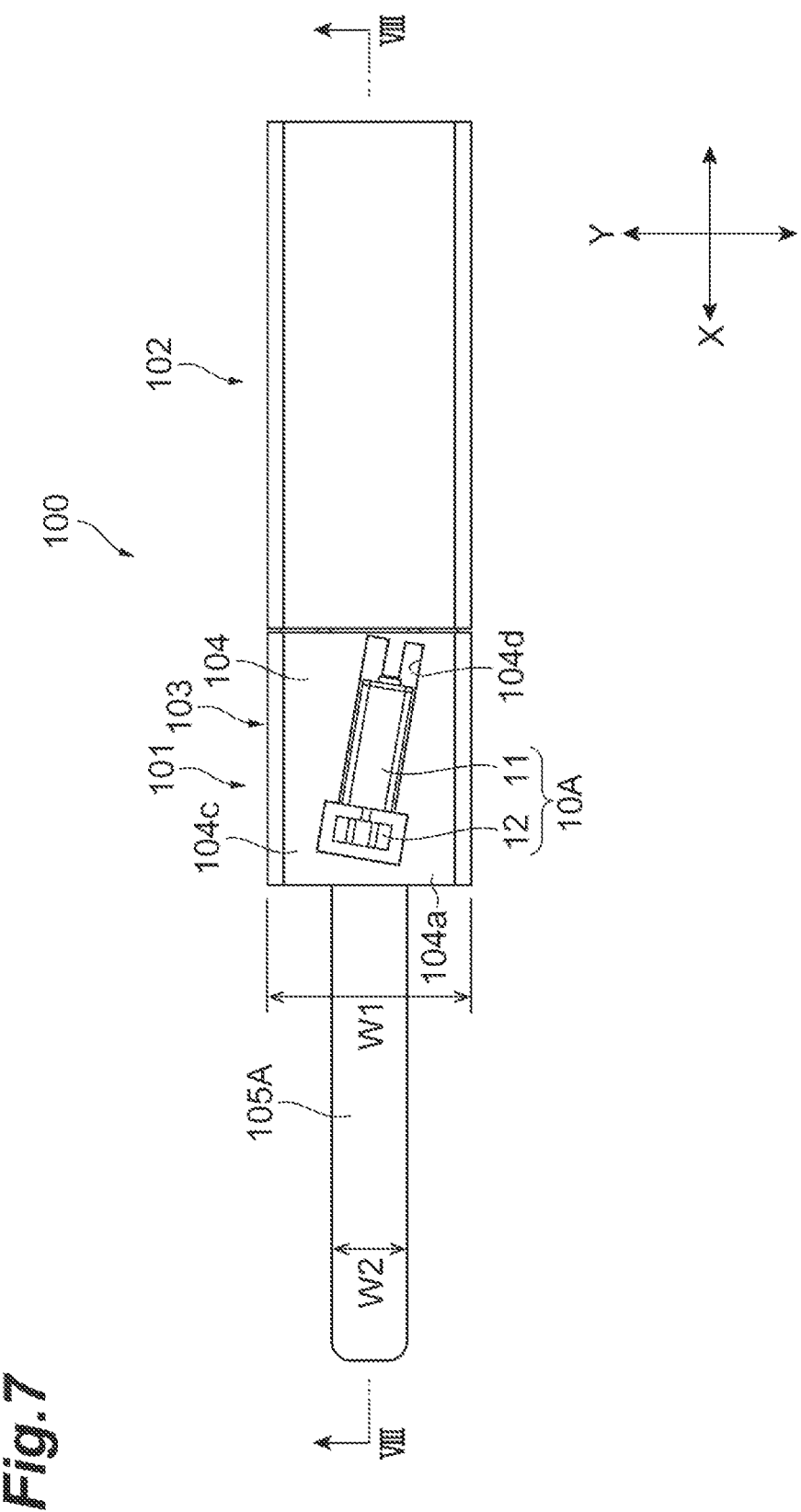
FIG. 7 is a plan view of a first device used in a verification experiment.
Figure 8:
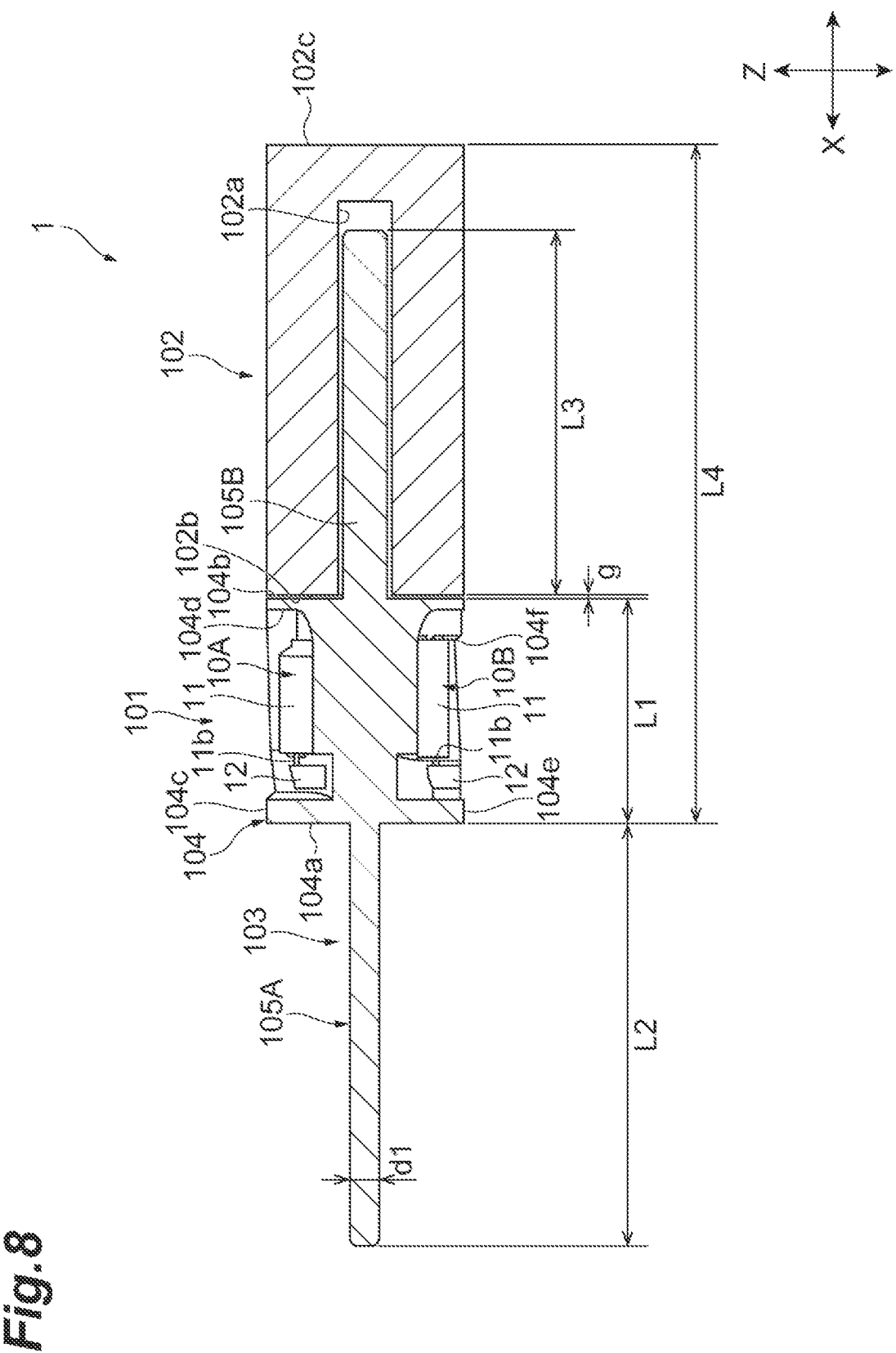
FIG. 8 is a cross-sectional view along line VIII-VIII in FIG. 7.
Figure 9:
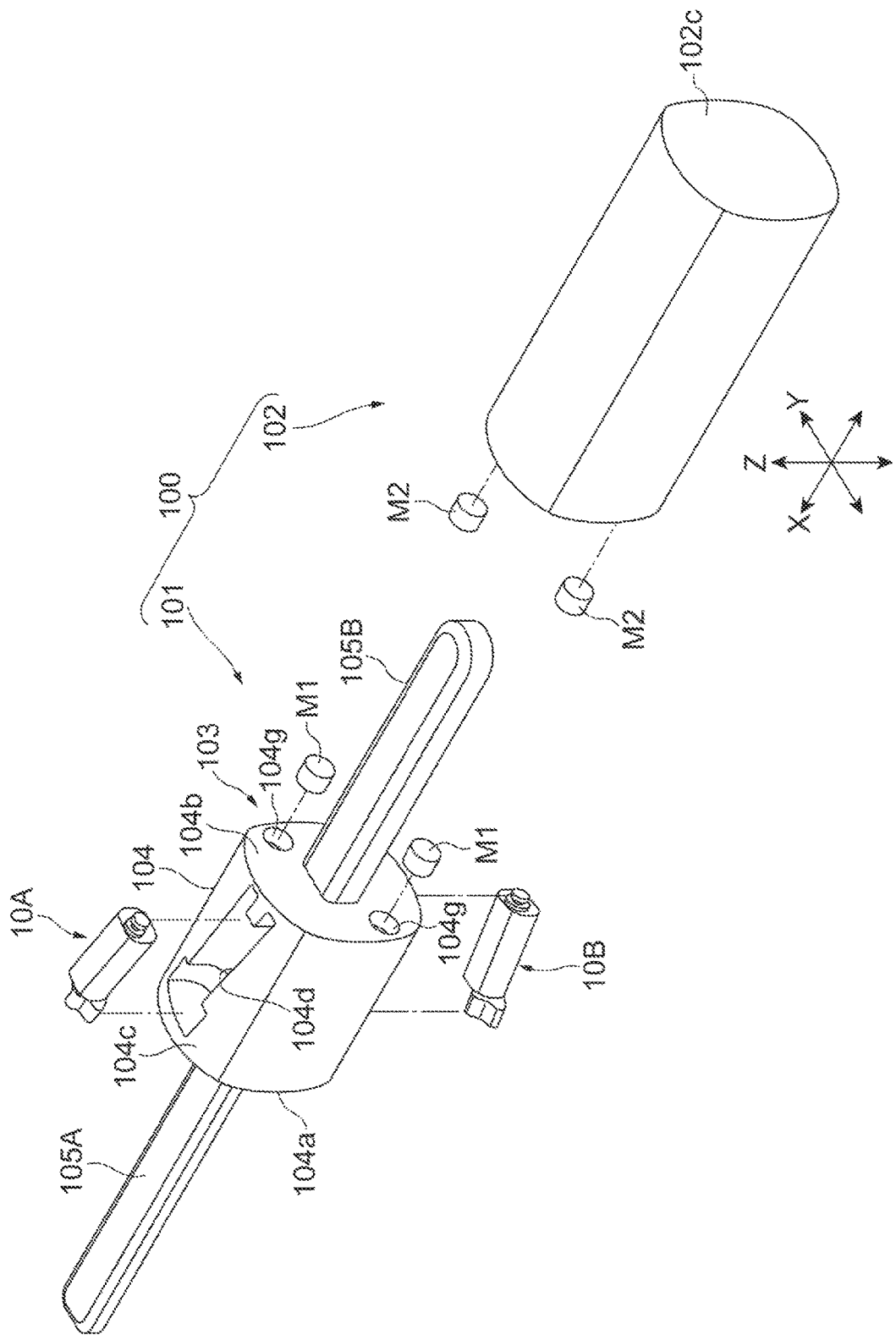
FIG. 9 is an exploded perspective view of the first device shown in FIG. 7.
Figure 10:
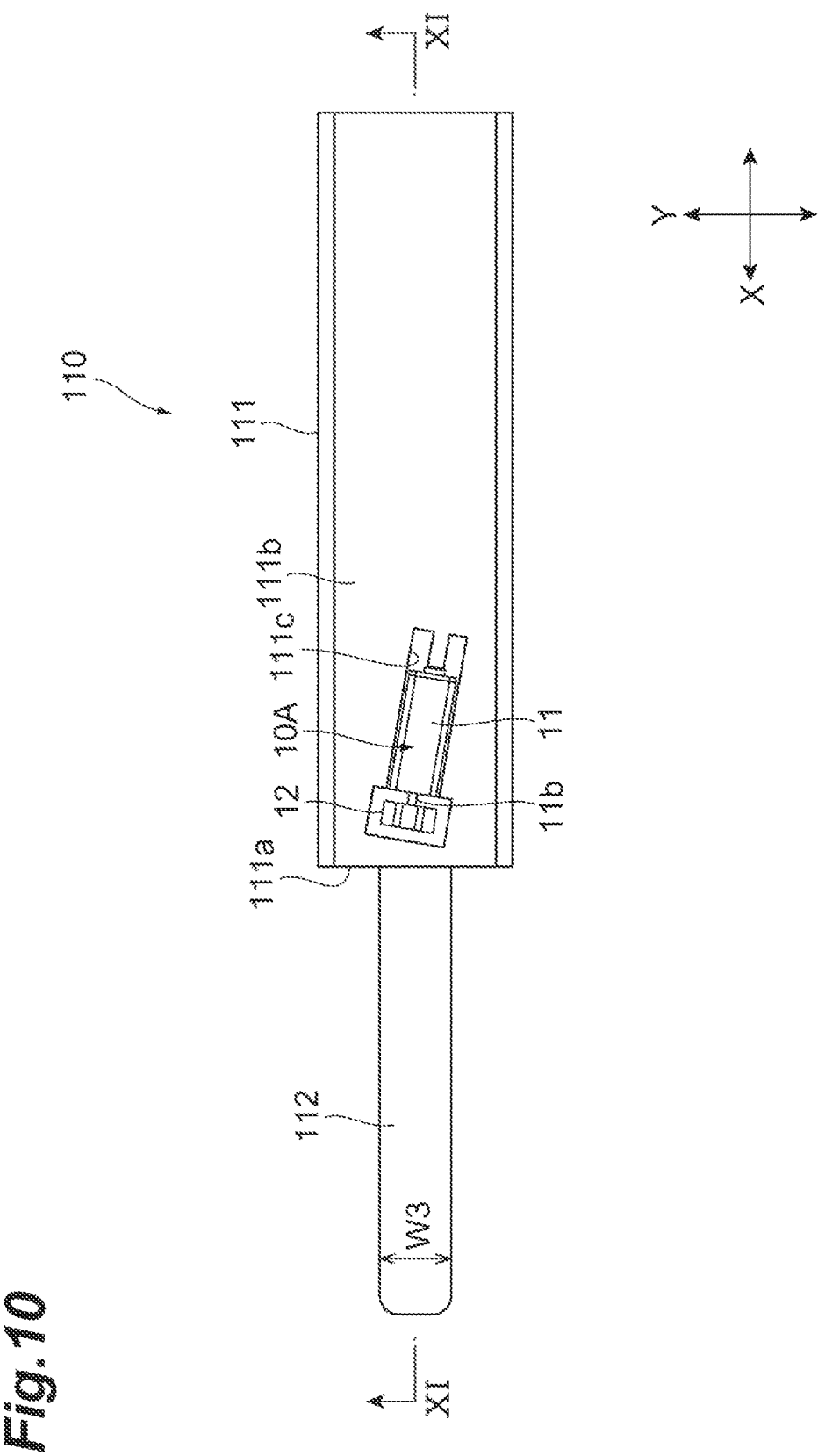
FIG. 10 is a plan view of a second device used in a verification experiment.
Figure 11:
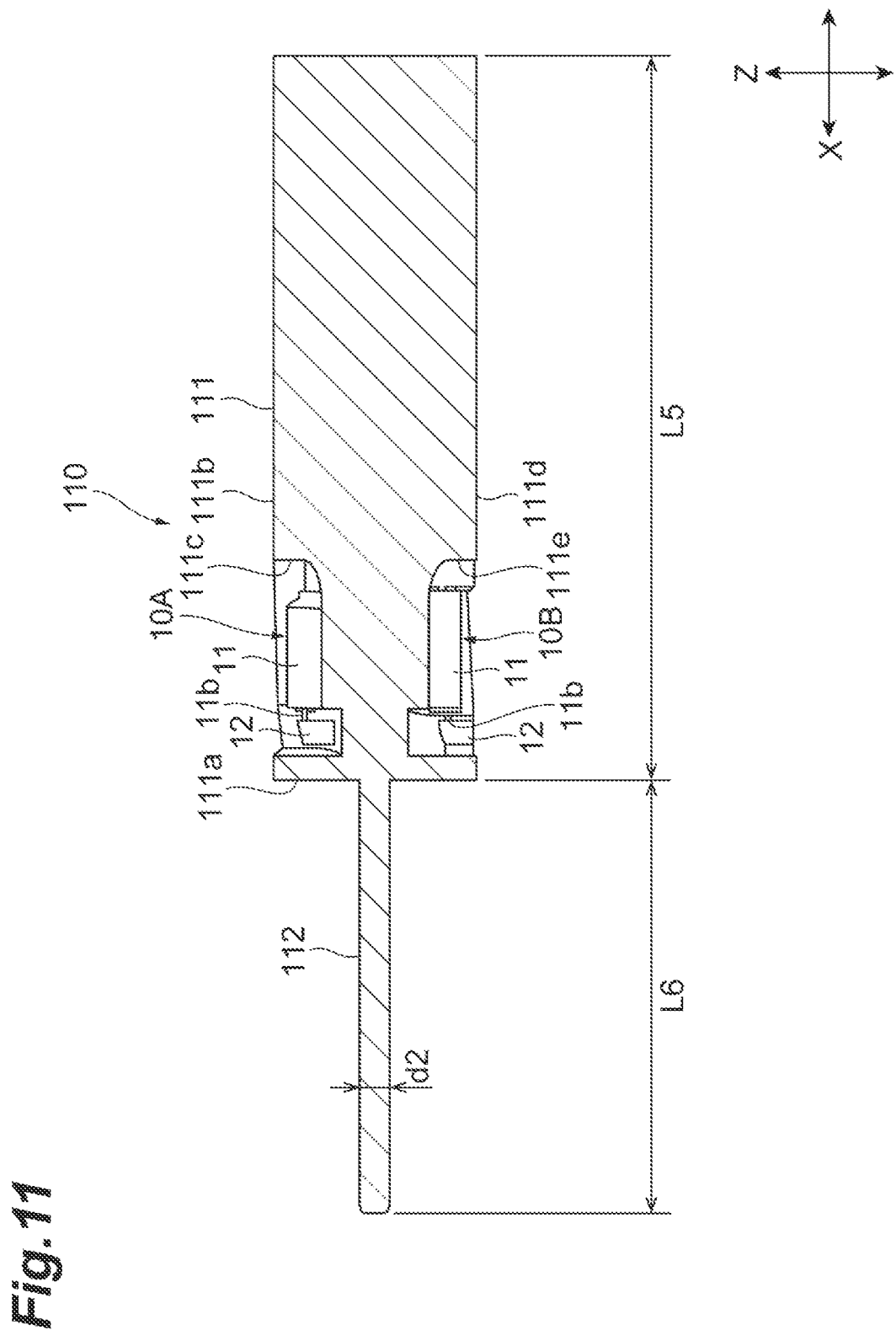
FIG. 11 is a cross-sectional view along line XI-XI in FIG. 10.

In the experiments, a first device 100 shown in FIG. 7 to FIG. 9 was used, and a second device 110 shown in FIG. 10 and FIG. 11 was used.

<First Device>

The first device 100 includes a first part 101 and a second part 102. The first part 101 and the second part 102 are configured to be attachable to and detachable from each other by magnetic force.

The first part 101 is a part that models the state in which the toothbrush 2 is inserted through and held by the vibration applicator 3. The first part 101 includes a main unit 103, vibration units 10A and 10B, and two first magnets M1 and M1.

The main unit 103 is configured such that rods 105A and 105B are erected on a pillar-shaped body 104. In the description of the first device 100, the axial direction of the pillar-shaped body 104 is referred to as the X-axis direction, and two directions orthogonal to the X-axis direction are referred to as the Y-axis direction and the Z-axis direction.

The pillar-shaped body 104 is approximately shaped like a rectangular parallelepiped. As shown in FIG. 8, the length L1 in the axial direction (X-axis direction) of the pillar-shaped body 104 was 40 mm. As shown in FIG. 7, the maximum width W1 of the pillar-shaped body 104 was 35 mm.

As shown in FIG. 8 and FIG. 9, the rods 105A and 105B were erected on the end surface 104a and the end surface 104b of the pillar-shaped body 104 such that the axes of the rods 105A and 105B matched with the axis of the pillar-shaped body 104. The length L2 of the rod 105A was 75 mm, the width W2 (see FIG. 7) of the rod 105A was 11.5 mm, and the thickness d1 of the rod 105A was 5 mm. The length L3 of the rod 105B was 65 mm. The material of the main unit 103 is polycarbonate (PC) and integrally molded.

The vibration unit 10A is housed in a depression 104d formed in the side surface 104c of the pillar-shaped body 104, and the eccentric weight 12 fixed to the shaft 11b of the motor 11 of the vibration unit 10A is rotatably fixed. The depression 104d is formed such that the direction in which the depression 104d extends crosses the axis of the pillar-shaped body 104. Thus, the axial direction of the motor 11 in the vibration unit 10A disposed and fixed in the depression 104d is inclined relative to the axis of the pillar-shaped body 104.

The vibration unit 10B is housed in a depression 104f formed in the side surface 104e on the opposite side to the side surface 104c similarly except that the axial direction of the motor 11 in the vibration unit 10B is inclined relative to the axis of the pillar-shaped body 104 on the opposite side to the axial direction of the motor 11 in the vibration unit 10A.

As shown in FIG. 9, the end surface 104b of the pillar-shaped body 104 has holes 104g in which the first magnets M1 are housed. The first magnets M1 are fixed in the holes 104g with adhesive. The first magnets M1 are provided on the lower left and the upper left when the end surface 104b is viewed from the second part 102, as shown in FIG. 9. The first magnet M1 was a disk-shaped permanent magnet.

The second part 102 is a pillar-shaped part that models the grip 4. As shown in FIG. 8, the second part 102 has an insertion hole 102a into which the rod 105B of the first part 101 is inserted. The shape of the cross section orthogonal to the axis of the second part 102 is approximately the same as the shape of the cross section orthogonal to the axis of the first part 101. The second part 102 is formed of polycarbonate (PC) in the same manner as the first part 101. The second magnets M2 were fixed at the positions corresponding to the first magnets M1 on the end surface 102b (see FIG. 8) of the second part 102. The second magnets M2 are housed in the depressions formed in the end surface 102b and fixed with adhesive, in the same manner as in the first magnets M1.

In a state in which the first part 101 is attached to the second part 102 by magnetic force of the first magnets M1 and the second magnets M2, the length L4 from the end surface 102c on the opposite side to the end surface 102b of the second part 102 to the end surface 104a of the first part 101 was 120 mm. A gap g of 0.6 mm existed between the first part 101 and the second part 102.

<Second Device>

The second device 110 includes a pillar-shaped body 111 and a rod 112 extending from the end surface 111a of the pillar-shaped body 111 along the axis of the pillar-shaped body 111. Also in the description of the second device 110, the axial direction of the pillar-shaped body 111 is referred to as the X-axis direction, and two directions orthogonal to the X-axis direction are referred to as the Y-axis direction and the Z-axis direction, in the same manner as in the first device 100. The length L5 in the X-axis direction of the pillar-shaped body 111 was 125 mm. The shape of the cross section orthogonal to the axial direction of the pillar-shaped body 111 was approximately the same as the cross-sectional shape of the pillar-shaped body 104 of the first device 100.

The length L6 of the rod 112 was 75 mm, the thickness d2 was 5 mm, and the width W3 (see FIG. 10) was 11.5 mm.

The pillar-shaped body 111 and the rod 112 are formed of polycarbonate (PC) in the same manner as the first part 101 and the second part 102, and the second device 110 is integrally molded.

The vibration unit 10A was fixed to the side surface 111b of the pillar-shaped body 111 in the same manner as the vibration unit 10A of the first device 100. That is, the vibration unit 10A was housed and fixed in a depression 111c formed in the side surface 111b.

Similarly, the vibration unit 10B is fixed to the side surface 111d on the opposite side to the side surface 111b of the pillar-shaped body 111, in the same manner as the vibration unit 10B of the first device 100. That is, the vibration unit 10B is housed and fixed in a depression 111e formed in the side surface 111d.

In a case where the end surface 111a in the pillar-shaped body 111 corresponded to the end surface 104a in the pillar-shaped body 104, the arrangement of the vibration units 10A and 10B in the second device 110 was the same as the vibration units 10A and 10B in the first device 100.

[Verification Experiment 1]

Figure 12:
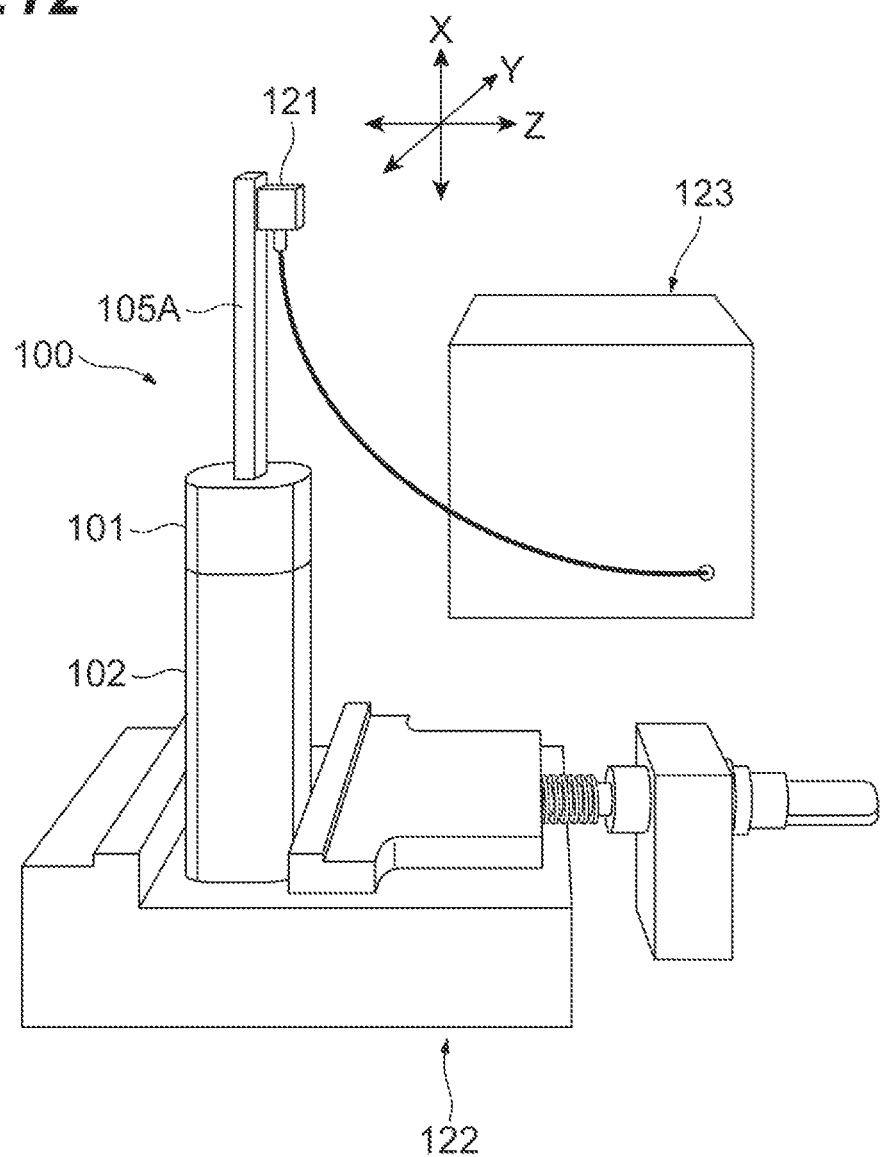
FIG. 12 is a diagram for explaining an experiment method in the verification experiment.

In Verification Experiment 1, as schematically shown in FIG. 12, the first part 101 was attached to the second part 102 by magnetic force of the first magnets M1 and the second magnets M2 to construct the first device 100. Subsequently, in the first device 100, with a vibration sensor 121 attached to a portion on the front-side end of the toothbrush 2 shown in FIG. 1 (that is, the tip end of the rod 105A of the first device 100), an end portion on the second part 102 side of the first device 100 was held with a vise 122 to fix the first device 100. The fixing with the vise 122 corresponds to the user holding the grip of the toothbrush vibrator. The vibration sensor 121 used was a three-axis acceleration detector with a built-in amplifier MODEL-2462 manufactured by Showa Sokki Corporation.

The motor 11 in the vibration unit 10A, of the vibration units 10A and 10B attached to the first device 100, was driven, and the vibration state of the tip end of the rod 105A was measured with the vibration sensor 121. That is, in Verification Experiment 1, one vibration unit 10A alone was used to vibrate the first device 100.

The displacement (mm) in each of the X-axis direction, the Y-axis direction, and the Z-axis direction shown in FIG. 12 as well as the acceleration (G) in each direction was measured as the vibration state of the first device 100. The X-axis direction corresponds to the axial direction of the first device 100, the Y-axis direction corresponds to the width direction of the rod 105A, and the Z-axis direction corresponds to the thickness direction of the rod 105A. The X-axis direction, the Y-axis direction, and the Z-axis direction shown in FIG. 12 correspond to the directions shown in FIG. 8 to FIG. 10.

The measurement results of the vibration sensor 121 were determined by a charge vibrometer Model-1607A manufactured by Showa Sokki Corporation as a vibrometer 123. Specifically, as previously mentioned, data of displacement and acceleration was obtained by switching the determination modes in a state in which the first device 100 was vibrated.

Figure 13:
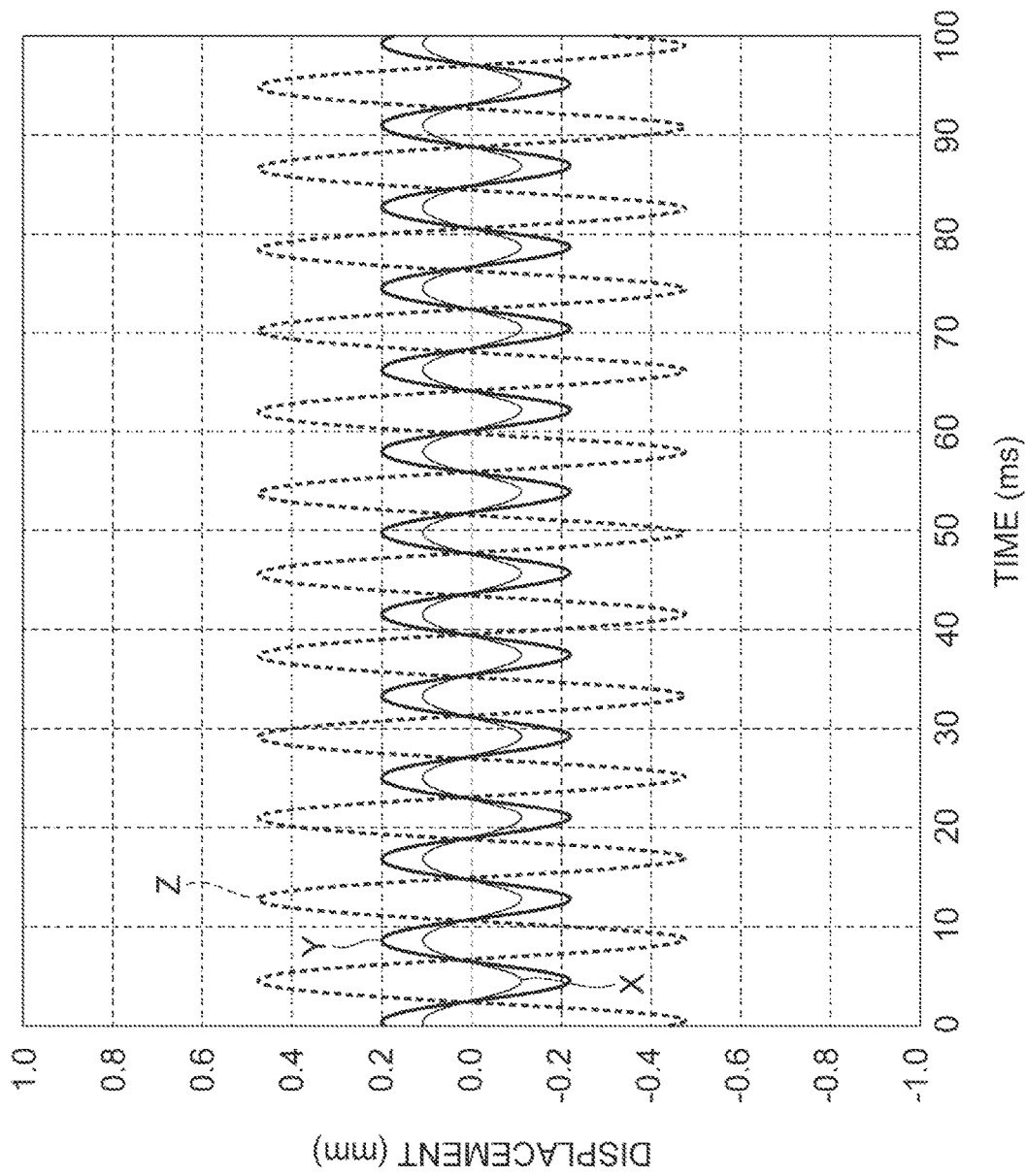
FIG. 13 is a diagram showing the experiment result when the displacement of the tip end portion of the first device that is associated with vibration of the first device was measured in Verification Experiment 1 in which the first device was used and one of two vibration units of the first device was driven.
Figure 14:
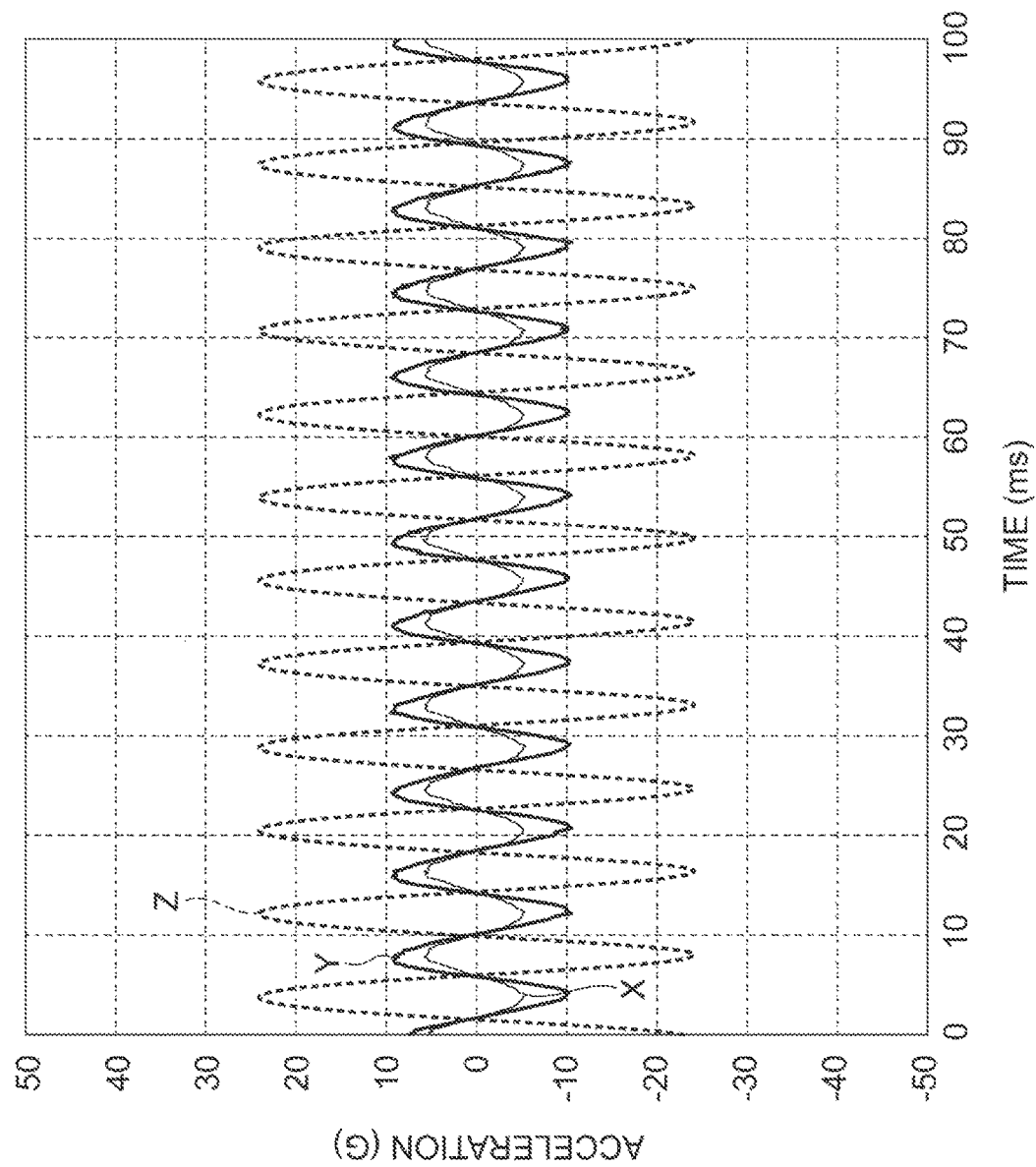
FIG. 14 is a diagram showing the experiment result when the acceleration of the tip end portion of the first device that is associated with vibration of the first device was measured in Verification Experiment 1.

The experiment result of displacement is as shown in FIG. 13. In FIG. 13, the horizontal axis shows the time (ms), and the vertical axis shows the displacement (mm). The experiment result of acceleration is as shown in FIG. 14. In FIG. 14, the horizontal axis shows the time (ms), and the vertical axis shows the acceleration (G).

[Verification Experiment 2]

Figure 15:
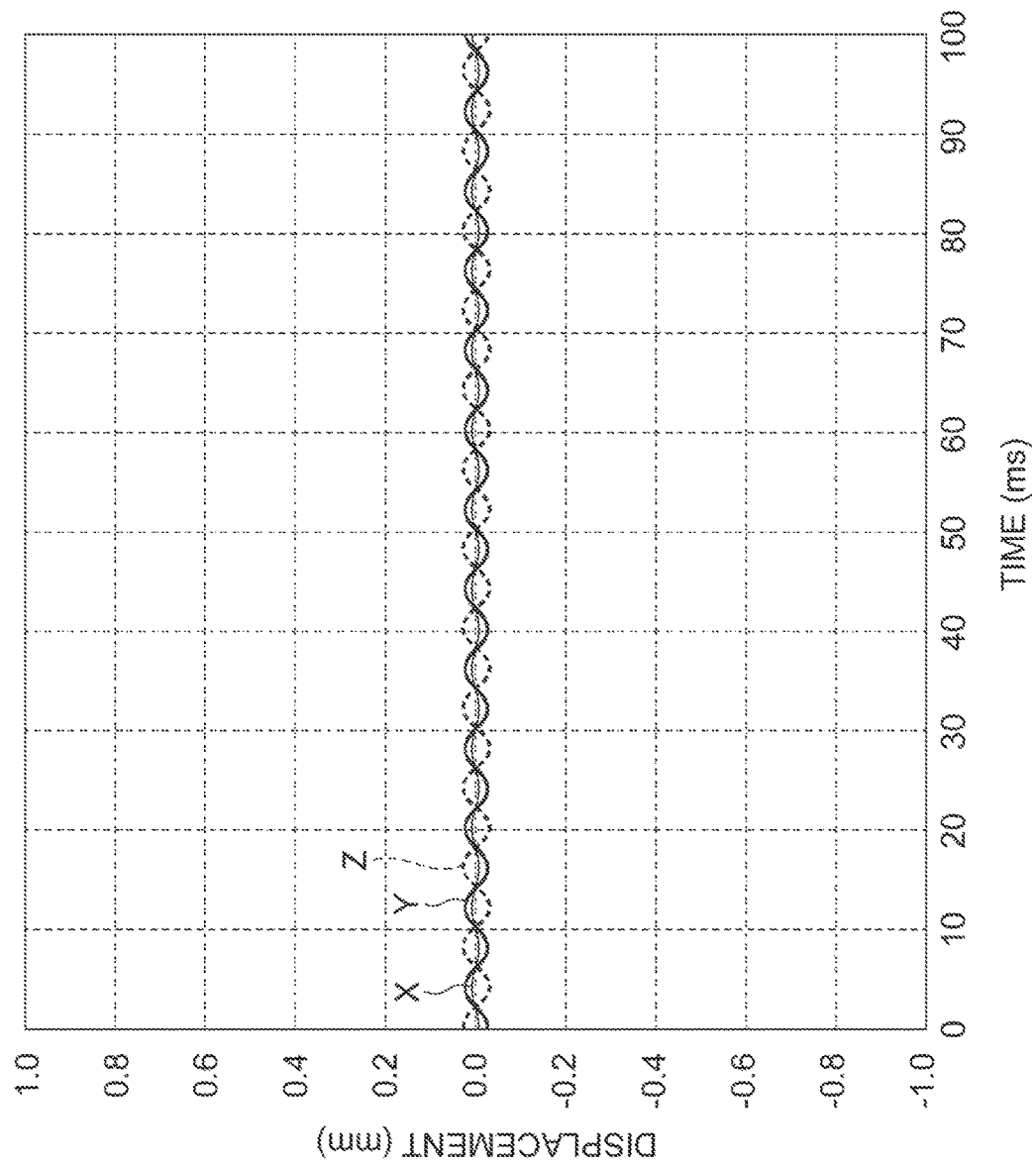
FIG. 15 is a diagram showing the experiment result when the displacement of the tip end portion of the second device that is associated with vibration of the second device was measured in Verification Experiment 2 in which the second device was used and one of two vibration units of the second device was driven.
Figure 16:
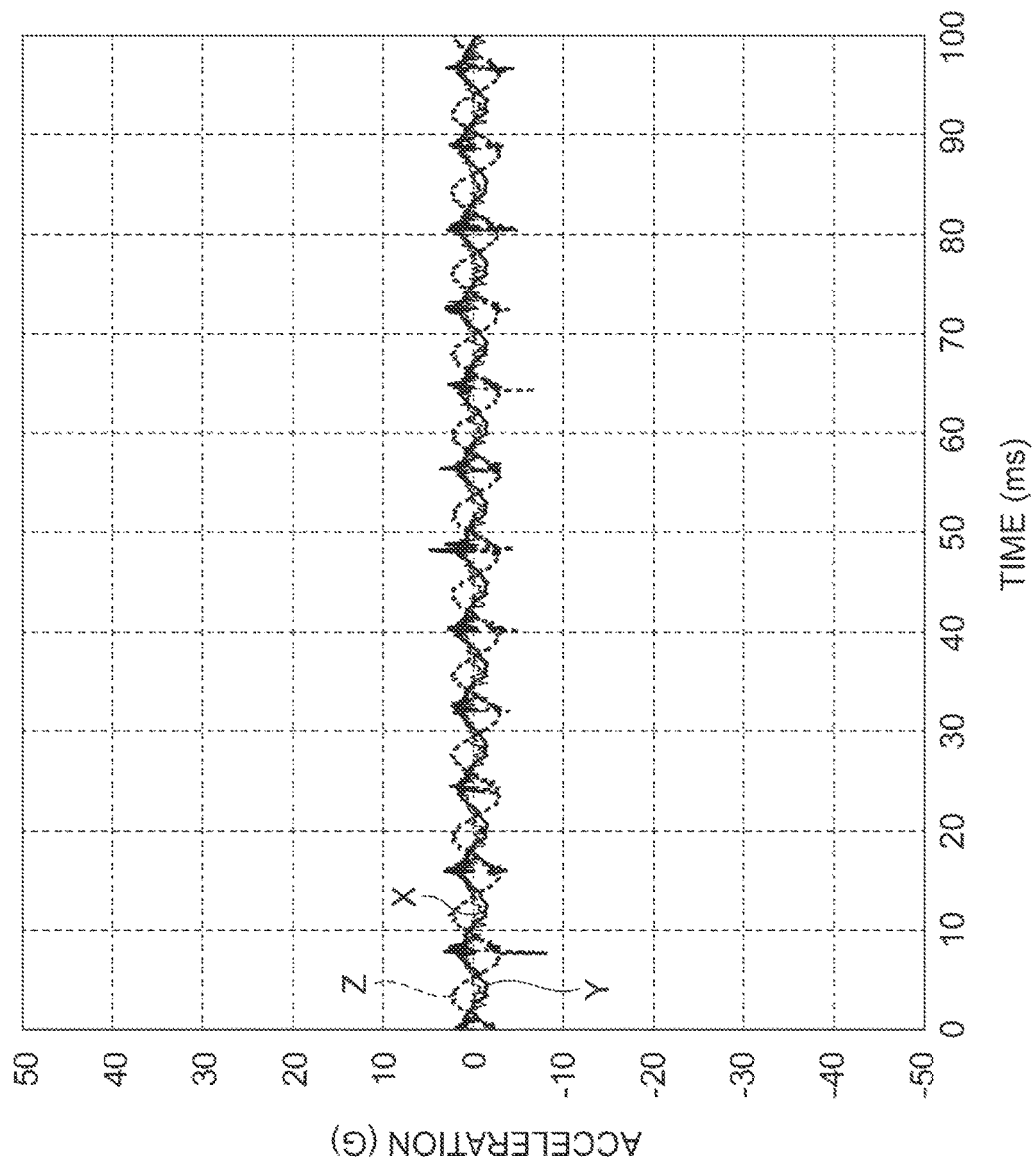
FIG. 16 is a diagram showing the experiment result when the acceleration of the tip end portion of the second device that is associated with vibration of the second device was measured in Verification Experiment 2.

An experiment similar to Verification Experiment 1 was conducted except that the second device 110 was fixed to the vise 122 instead of the first device 100. In the second device 110, the vibration sensor 121 was attached to the tip end of the rod 112. The experiment result of displacement is as shown in FIG. 15. In FIG. 15, the horizontal axis shows the time (ms), and the vertical axis shows the displacement (mm). The experiment result of acceleration is as shown in FIG. 16. In FIG. 16, the horizontal axis shows the time (ms), and the vertical axis shows the acceleration (G).

[Comparison between Verification Experiment 1 and Verification Experiment 2]

The comparison between FIG. 13 and FIG. 15 showing the measurement results of displacement shows that the first device 100 including the first part 101 and the second part 102 attachable to and detachable from each other achieves a larger displacement than the second device 110 in all of the X-axis direction, the Y-axis direction, and the Z-axis direction. The comparison between FIG. 14 and FIG. 16 showing the measurement results of acceleration also shows that the first device 100 achieves a larger acceleration than the integrated second device 110 in all of the X-axis direction, the Y-axis direction, and the Z-axis direction.

The first device 100 includes the first part 101 having the vibration unit 10A attached thereto and the second part 102 and is configured such that these parts are attachable to and detachable from each other. Thus, the first device 100 corresponds to the vibrator 1 shown in FIG. 1. In contrast, the second device 110 corresponds to a model in which the first part 101 and the second part 102 in the first device 100 are integrated so as not to be separated. In other words, the second device 110 corresponds to the conventional electric toothbrush model. Then, as previously mentioned, fixing the respective one ends of the first device 100 and the second device 110 with the vise 122 corresponds to the user holding the grip.

Based on the results of Verification Experiment 1 and Verification Experiment 2, it has been verified that attenuation of vibration by the vibration unit 10A can be reduced with the configuration in which the vibration applicator 3 and the grip 4 are attachable to and detachable from each other, compared with the electric toothbrush having the vibration unit disposed at the portion gripped by the user and tightly attached thereto as in the conventional example.

[Verification Experiment 3]

Figure 17:
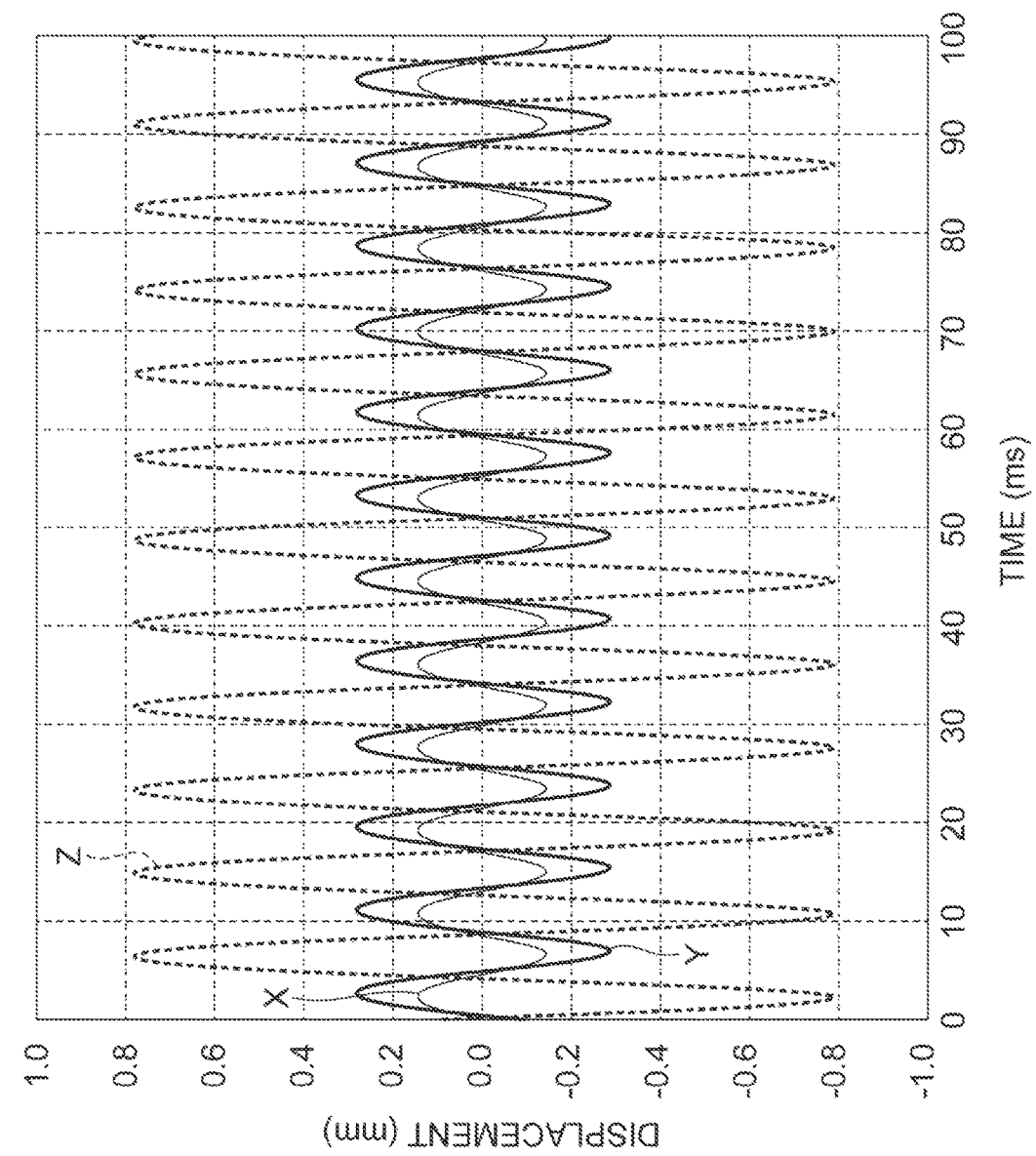
FIG. 17 is a diagram showing the experiment result when the displacement of the tip end portion of the first device that is associated with vibration of the first device was measured in Verification Experiment 3 in which the first device was used and two vibration units of the first device were driven.
Figure 18:
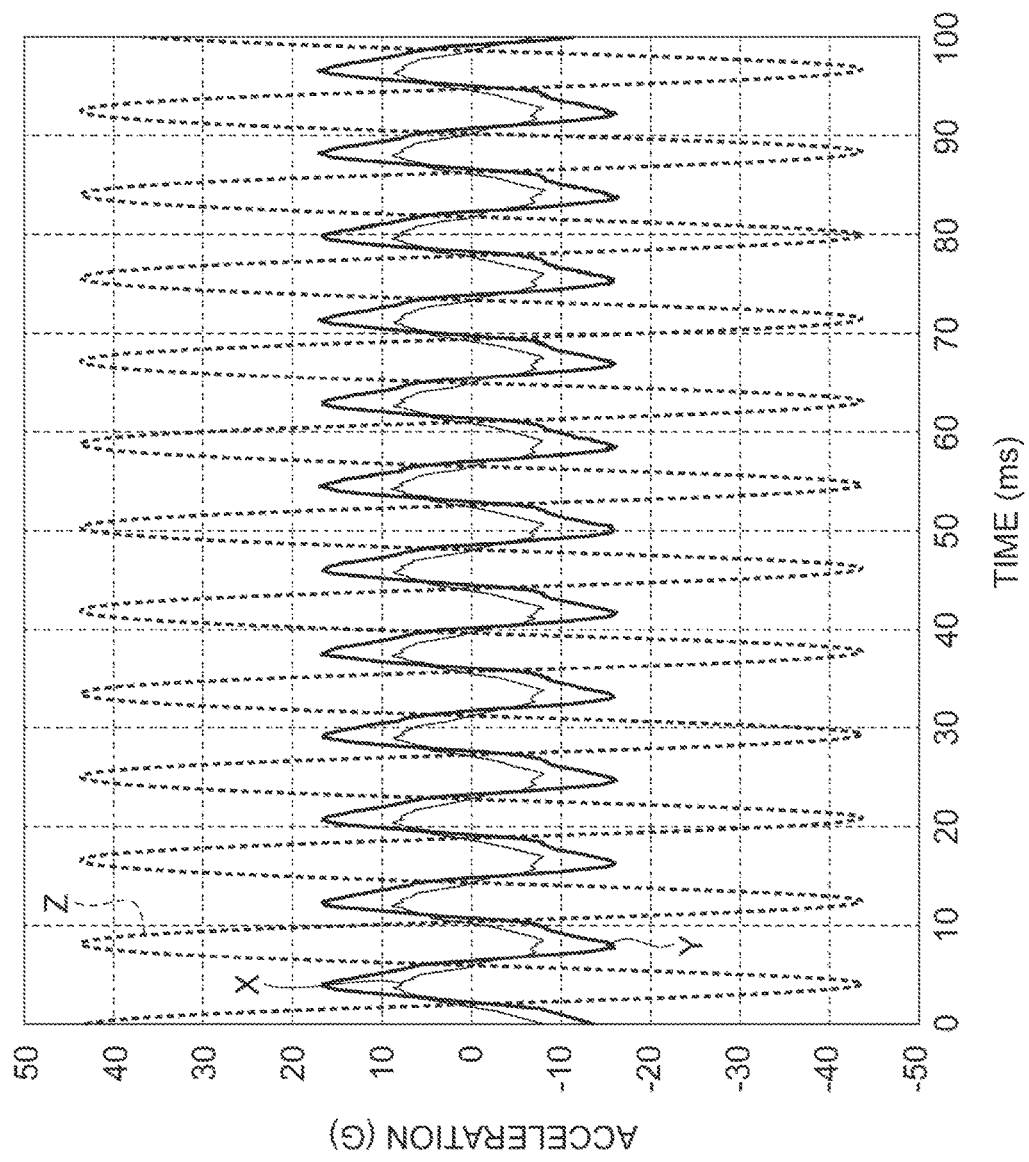
FIG. 18 is a diagram showing the experiment result when the acceleration of the tip end portion of the first device that is associated with vibration of the first device was measured in Verification Experiment 3.

In Verification Experiment 3, an experiment was conducted in the same manner as Verification Experiment 1, except that two vibration units 10A and 10B were driven in Verification Experiment 1. The experiment result of displacement is as shown in FIG. 17. In FIG. 17, the horizontal axis shows the time (ms), and the vertical axis shows the displacement (mm). The experiment result of acceleration is as shown in FIG. 18. In FIG. 18, the horizontal axis shows the time (ms), and the vertical axis shows the acceleration (G).

[Verification Experiment 4]

Figure 19:
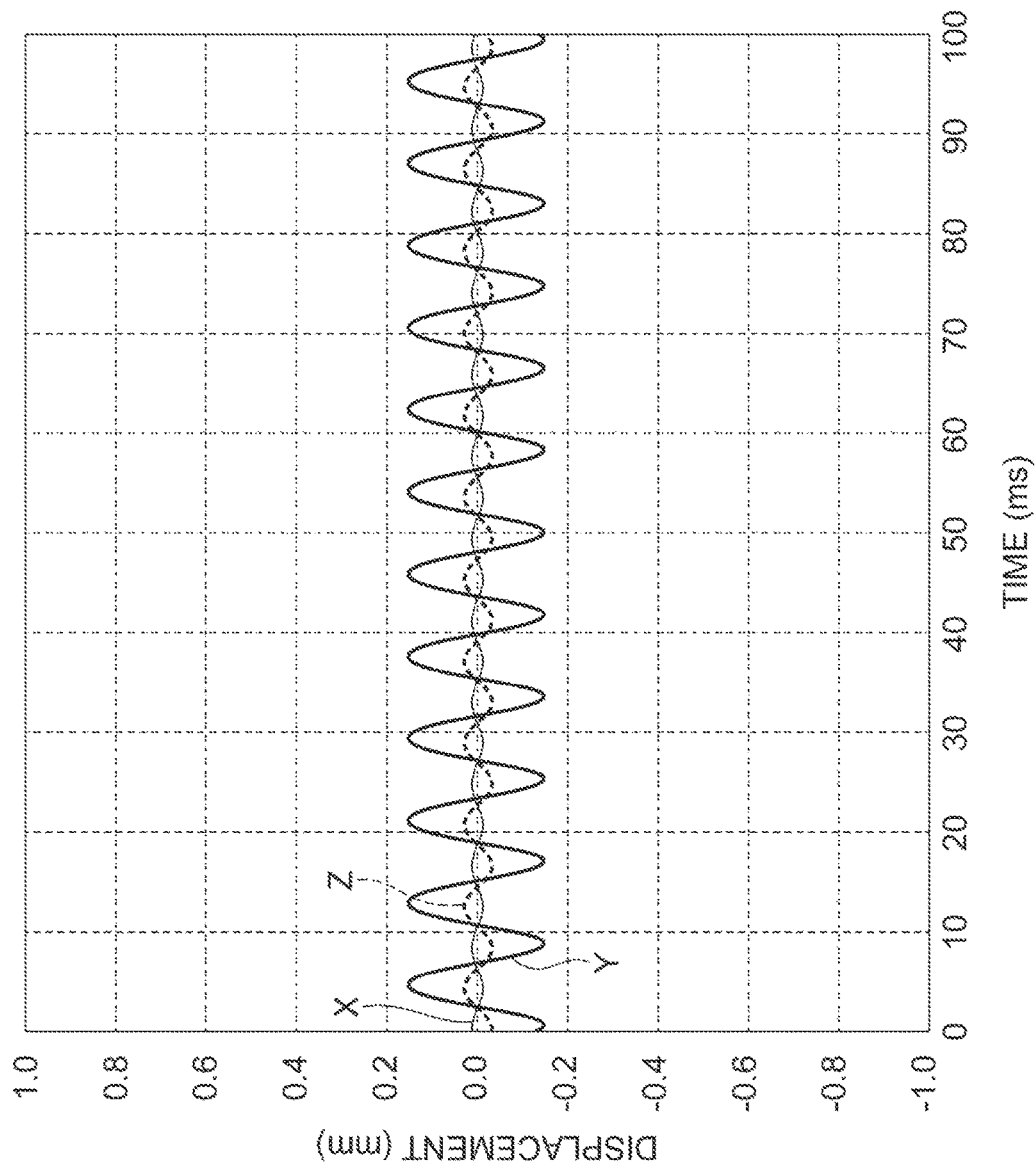
FIG. 19 is a diagram showing the experiment result when the displacement of the tip end portion of the second device that is associated with vibration of the second device was measured in Verification Experiment 4 in which the second device was used and two vibration units of the second device were driven.
Figure 20:
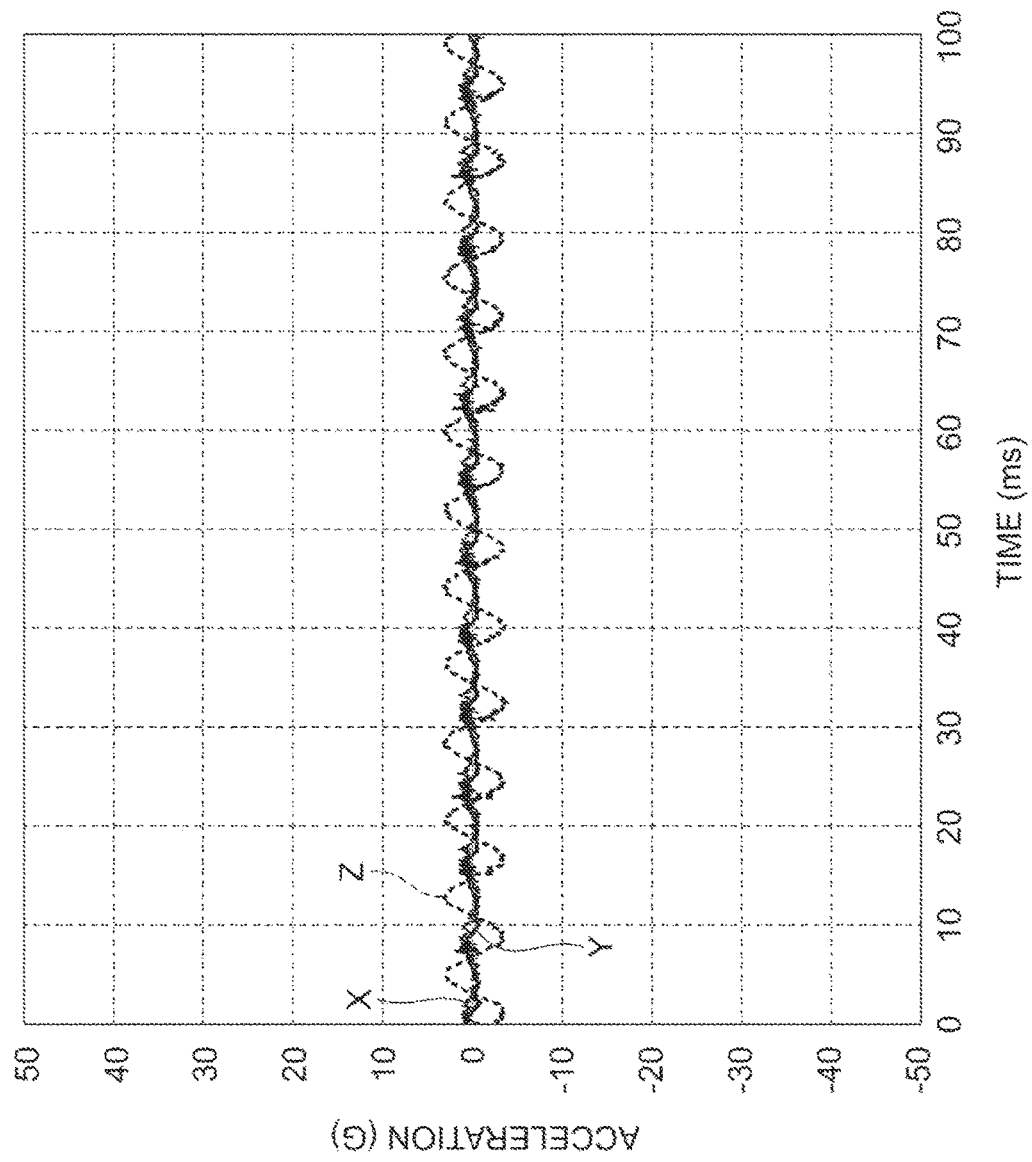
FIG. 20 is a diagram showing the experiment result when the acceleration of the tip end portion of the second device that is associated with vibration of the second device was measured in Verification Experiment 4.

In Verification Experiment 4, an experiment was conducted in the same manner as Verification Experiment 2, except that two vibration units 10A and 10B were driven in Verification Experiment 2. The arrangement position of the vibration sensor 121 is as described in Verification Experiment 2. The experiment result of displacement is as shown in FIG. 19. In FIG. 19, the horizontal axis shows the time (ms), and the vertical axis shows the displacement (mm). The experiment result of acceleration is as shown in FIG. 20. In FIG. 20, the horizontal axis shows the time (ms), and the vertical axis shows the acceleration (G).

[Comparison between Verification Experiment 3 and Verification Experiment 4]

The comparison between FIG. 17 and FIG. 19 showing the measurement results of displacement shows that the first device 100 achieves a larger displacement than the second device 110 in all of the X-axis direction, the Y-axis direction, and the Z-axis direction. The comparison between FIG. 18 and FIG. 20 showing the measurement results of acceleration also shows that the first device 100 achieves a larger acceleration than the second device 110 in all of the X-axis direction, the Y-axis direction, and the Z-axis direction.

It has been verified that when two vibration units 10A and 10B are driven, attenuation of the vibration by the vibration units 10A and 10B can be reduced with the configuration in which the vibration applicator 3 and the grip 4 are attachable to and detachable from each other, compared with the electric toothbrush having the vibration unit disposed at the portion gripped by the user and tightly attached thereto as in the conventional example.

[Comparison between Verification Experiment 1 and Verification Experiment 3]

In both of Verification Experiment 1 and Verification Experiment 3, the first device 100 corresponding to the vibrator 1 was used for experiments. The difference between Verification Experiment 1 and Verification Experiment 3 is that, of the vibration units 10A and 10B, the vibration unit 10A alone is driven in Verification Experiment 1, whereas both of the vibration units 10A and 10B are driven in Verification Experiment 3.

The comparison between FIG. 13 and FIG. 17 showing the measurement results of displacement in Verification Experiment 1 and Verification Experiment 3 shows that Verification Experiment 3 achieves a larger displacement than Verification Experiment 1 in all of the X-axis direction, the Y-axis direction, and the Z-axis direction. The comparison between FIG. 14 and FIG. 18 showing the measurement results of acceleration in Verification Experiment 1 and Verification Experiment 3 shows that Verification Experiment 3 achieves a larger acceleration than Verification Experiment 1 in all of the X-axis direction, the Y-axis direction, and the Z-axis direction. That is, it has been verified that the vibrator 1 can be vibrated more efficiently by being driven with two vibration units 10A and 10B than by being driven with one vibration unit 10A.

(Second Embodiment)

A vibrator 1A for toothbrushes according to a second embodiment shown in FIG. 21 will now be described. Also in the second embodiment, the vibrator 1A for toothbrushes is referred to as vibrator 1A.

The vibrator 1A is a toothbrush holder similar to the first embodiment. The vibrator 1A includes a vibration applicator 5 and a grip 6. The vibration applicator 5 and the grip 6 are separate parts attachable to and detachable from each other, as in the first embodiment.

The vibration applicator 5 includes two vibration units 10A and 10B, as in the vibration applicator 3 of the vibrator 1. Also in the second embodiment, the vibration units 10A and 10B are eccentric weighted motors including an eccentric weight 12 eccentrically fixed to the shaft 11b of the motor 11.

The grip 6 includes a power supply unit 20 (see FIG. 4) electrically connected to the vibration units 10A and 10B in a state in which the vibration applicator 5 is attached to the grip 6, in the same manner as in the grip 4 of the vibrator 1. The grip 6 may include a vibration state display unit 30 (see FIG. 4). The electrical connection relationship between the vibration units 10A and 10B, the power supply unit 20, and the vibration state display unit 30 is similar to that of the vibrator 1 described with reference to FIG. 4 and will not be further elaborated here. Also in the second embodiment, the manner in which the vibration controller 23 drives the vibration units 10A and 10B such that they attain a similar vibration state will be mainly described. However, the vibration controller 23 may drive the vibration units 10A and 10B in different vibration states. That is, the vibration controller 23 may control such that one of the vibration unit 10A and the vibration unit 10B is driven and the other is not driven.

The vibrator 1A differs from the vibrator 1 mainly in that it is configured such that the single vibration applicator 5 can hold each of toothbrushes 2 with different sizes. Focusing on this difference, a manner in which the grip 6 includes the vibration state display unit 30 and the vibration state display unit 30 includes three LEDs 30a, 30b, and 30c will be described.

Also in the second embodiment, the bristles 2b side in the direction in which the handle 2a of the toothbrush 2 extends is referred to as the "front side", and the opposite side is referred to as the "rear side", as in the first embodiment. In the thickness direction of the handle 2a of the toothbrush 2, the side provided with the bristles 2b is referred to as the "front surface side", and the opposite side is referred to as the "rear surface side". In the description of the vibrator 1A, the aforementioned terms denoting the directions will be used, based on the state in which the toothbrush 2 is attached to the vibrator 1.

<Vibration Applicator>

Figure 21:
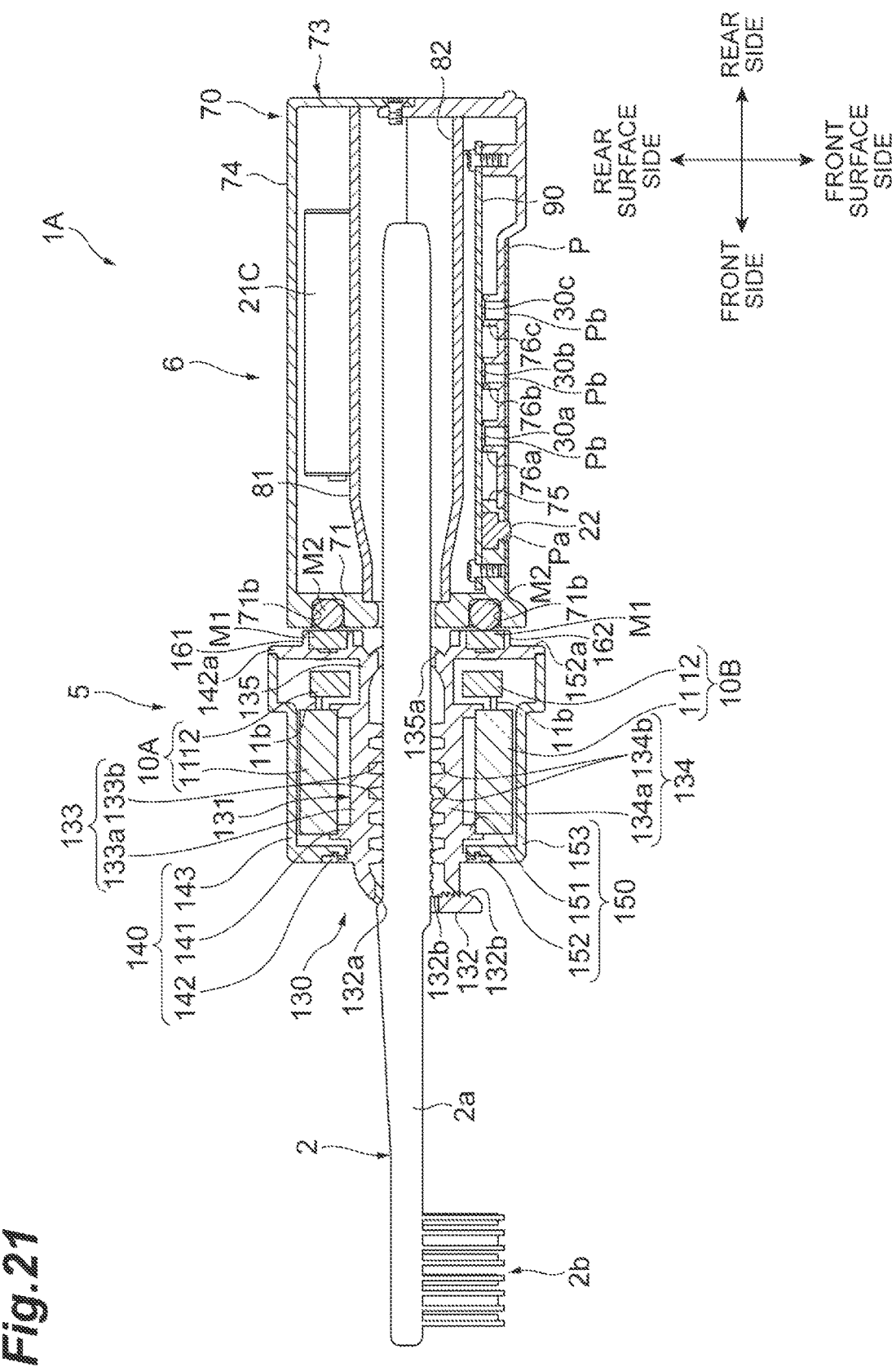
FIG. 21 is a longitudinal cross-sectional view schematically showing the configuration of a toothbrush vibrator according to a second embodiment.
Figure 22:
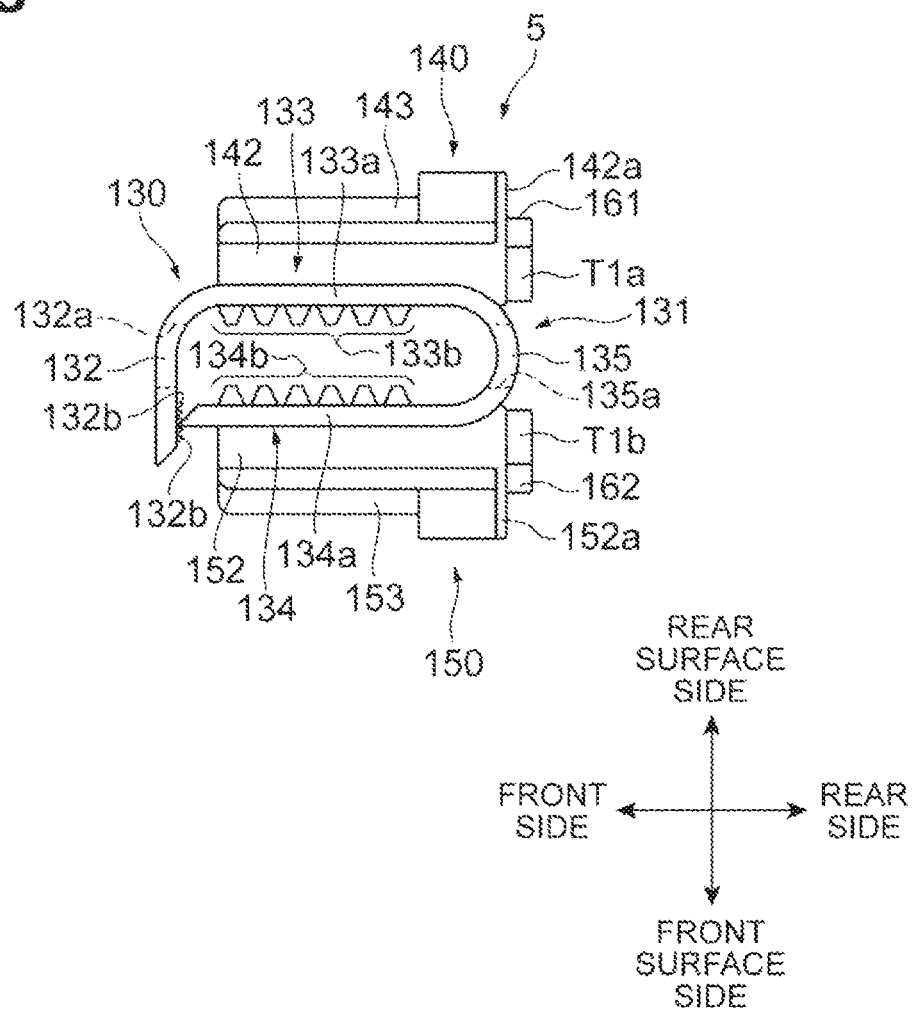
FIG. 22 is a diagram showing the vibration applicator of the toothbrush vibrator shown in FIG. 21 as viewed from the side.
Figure 23:
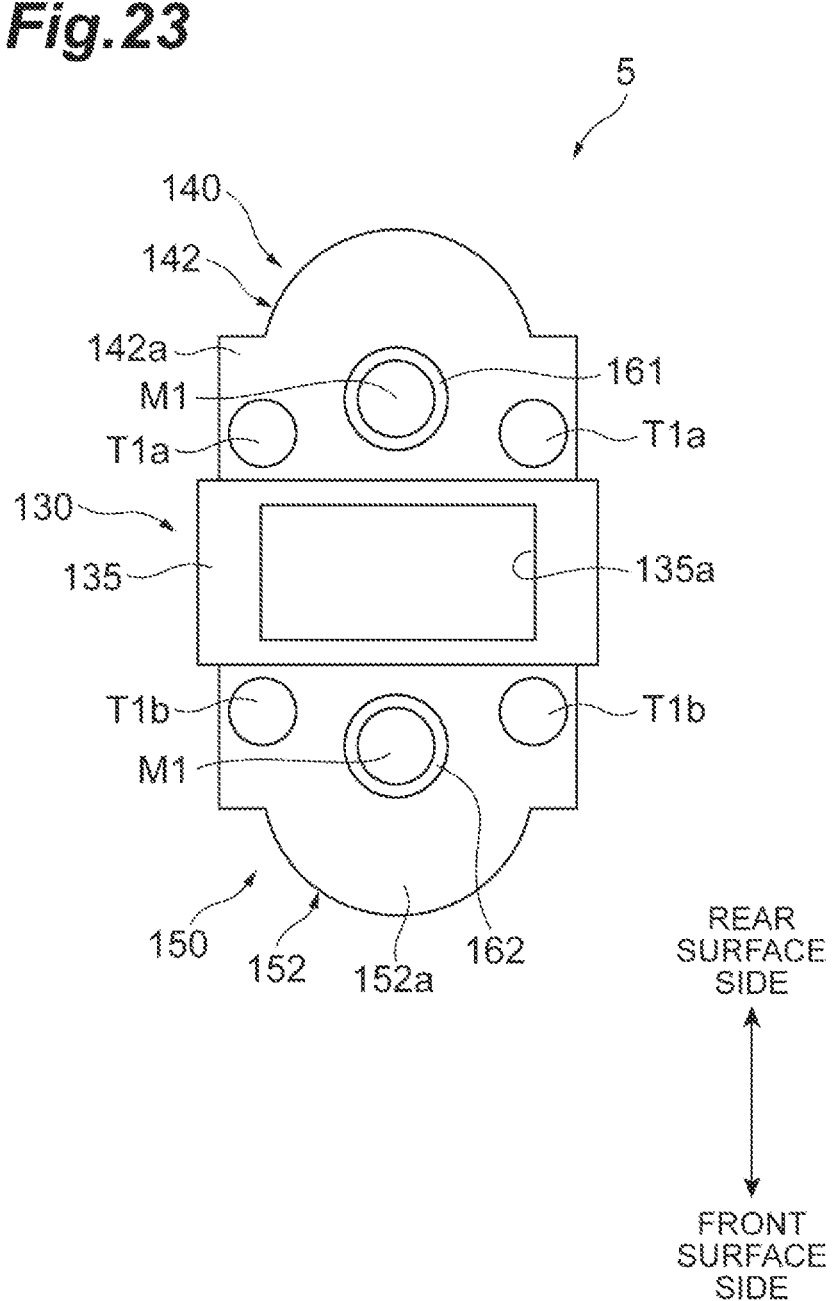
FIG. 23 is a diagram showing the vibration applicator of the toothbrush vibrator shown in FIG. 21 as viewed from the grip.

Referring to FIG. 21, FIG. 22, and FIG. 23, the vibration applicator 5 in the vibrator 1A will be described.

The vibration applicator 5 includes vibration units 10A and 10B, a toothbrush support 130, a first housing 140 for the vibration unit 10A, a second housing 150 for the vibration unit 10B, contact terminals T1a, T1a, T1b, and T1b, and first magnets M1 and M1.

The toothbrush support 130 includes a U-shaped member 131 and an end plate 132. The U-shaped member 131 is configured such that the rear ends of a first holding portion 133 and a second holding portion 134 opposed to each other are joined by a joint portion 135. The end plate 132 is provided at the front end of the first holding portion 133 to extend toward the second holding portion 134.

The end plate 132 and the joint portion 135 have a first opening 132a and a second opening 135a, respectively, to allow the handle 2a of the toothbrush 2 to pass through. The first opening 132a and the second opening 135a may be of size and shape such that all of the handles 2a of a plurality of possible toothbrushes 2 can pass through.

The toothbrush support 130 supports the toothbrush 2 such that the handle 2a inserted through the first opening 132a and the second opening 135a is sandwiched between the first holding portion 133 and the second holding portion 134. That is, the toothbrush support 130 functions as a clip for the toothbrush 2. A configuration example of the U-shaped member 131 and the end plate 132 will be specifically described below.

The first holding portion 133 of the U-shaped member 131 includes a first base plate 133a and a plurality of first projections 133b. The width of the first base plate 133a (the width as viewed from the thickness direction of the first base plate 133a) has a length necessary for holding the handle 2a of the toothbrush 2. For example, the width of the first base plate 133a may be equal to or greater than the width of the handle 2a of the toothbrush 2. An example of the material of the first base plate 133a is resin, and examples of the resin are DURACON resin and polypropylene (PP) resin.

A plurality of first projections 133b are provided on the inner surface of the first base plate 133a (the surface opposed to the second holding portion 134). Each first projection 133b extends in the width direction of the first base plate 133a, and a plurality of first projections 133b are discretely disposed in the direction orthogonal to the direction in which the first projection 133b extends. At least some of a plurality of first projections 133b come into abutment with the handle 2a when the handle 2a is sandwiched between the first holding portion 133 and the second holding portion 134. Examples of the shape of the cross section orthogonal to the direction in which the first projection 133b extends include a trapezoid, a rectangle, and a square.

Examples of the material of the first projections 133b include elastic materials such as rubber and the same material as the first base plate 133a. In the manner in which the material of the first projections 133b is the same as the first base plate 133a, a plurality of first projections 133b and the first base plate 133a may be integrally molded.

The second holding portion 134 of the U-shaped member 131 has the same configuration as the first holding portion 133. That is, the second holding portion 134 includes a second base plate 134a and a plurality of second projections 134b. The second base plate 134a and the second projections 134b have the same configuration as the first base plate 133a and the first projections 133b of the first holding portion 133. The front end of the second base plate 134a is formed to be engaged with a stopper portion 132b described later and is formed to have a triangular shape in a side surface view in the manner illustrated in FIG. 21 and FIG. 22.

The joint portion 135 is a plate that joins the rear ends of the first base plate 133a and the second base plate 134a. The joint portion 135 has the second opening 135a. Examples of the material of the joint portion 135 are similar to the examples of the material of the first base plate 133a. In the manner in which the joint portion 135, the first base plate 133a, and the second base plate 134a are formed of the same material, they may be integrally molded.

The end plate 132 is provided at the front end of the first base plate 133a to extend toward the second base plate 134a. At the end portion on the second base plate 134a side of the end plate 132, a plurality of stopper portions 132b are formed for locking the front end of the second base plate 134a. An example of the material of the end plate 132 is resin, and examples of the resin are DURACON resin and polypropylene (PP) resin. When the end plate 132 and the first base plate 133a are formed of the same material, they may be integrally molded.

Each stopper portion 132b extends in the width direction of the end plate 132. Although FIG. 21 and FIG. 22 illustrate the stopper portions 132b that protrude relative to the surface on the U-shaped member 131 side of the end plate 132, the stopper portions 132b may form recesses. A plurality of stopper portions 132b are discretely disposed in the direction orthogonal to the width direction of the end plate 132. The cross section orthogonal to the direction in which the stopper portion 132b extends has any shape that allows the front end of the second base plate 134a to be locked with the stopper portions 132b at different places.

In the aforementioned toothbrush support 130, the distance between the first base plate 133a and the second base plate 134a can be adjusted by appropriately selecting the position of the stopper portion 132b that locks the front end of the second base plate 134a. The toothbrush support 130 thus can support a plurality of toothbrushes 2 different in thickness of the handle 2a. Therefore, it is enough that the distance between a plurality of stopper portions 132b and the formation region thereof are set in accordance with the sizes of the handles 2a of a plurality of possible toothbrushes 2.

The first housing 140 is provided on the rear surface side of the U-shaped member 131 and includes a support base 141, a frame 142, and a cover 143.

The support base 141 is a base for supporting the vibration unit 10A and is fixed to the outer surface of the first base plate 133a. The motor 11 of the vibration unit 10A is fixed to the support base 141. The support base 141 may have any height that does not interfere with the rotation of the eccentric weight 12. Examples of the material of the support base 141 may be similar to the material of the first base plate 133a. In the manner in which the support base 141 is formed of the same material as the first base plate 133a, the first base plate 133a and the support base 141 may be integrally molded.

The frame 142 is fixed on the rear surface side of the U-shaped member 131 so as to surround the support base 141. The material of the frame 142 may be similar to the examples of the material of the first base plate 133a. In the manner in which the frame 142 is formed of the same material as the first base plate 133a, the first base plate 133a and the frame 142 may be integrally molded.

The cover 143 closes the end portion (the open end portion) on the opposite side to the first base plate 133a in the frame 142. The cover 143 is preferably detachably attached to the frame 142, for example, for replacement of the vibration unit 10A. The cover 143 may be fixed to the frame 142, for example, by screwing. An example of the material of the cover 143 is resin, and examples of the resin for the cover 143 include DURACON resin.

The second housing 150 is provided on the front surface side of the U-shaped member 131 and includes a support base 151, a frame 152, and a cover 153. The support base 151, the frame 152, and the cover 153 have the same configuration as the support base 141, the frame 142, and the cover 143 of the first housing 140.

As shown in FIG. 21 and FIG. 23, the contact terminal T1a and the contact terminal T1b are fixed to the rear walls 142a and 152a of the frame 142 and the frame 152, respectively. The contact terminal T1a may be configured to establish electrical connection between the contact terminal T2a and the vibration unit 10A. For example, the contact terminal T1a may be shaped like a screw (or bolt) and fixed to the rear wall 142a such that a shaft with a head passes through the rear wall 142a of the frame 142. Similarly, the contact terminal T1b is configured to establish electrical connection between the contact terminal T2b and the vibration unit 10B.

Two first magnets M1 are fixed to the rear walls 142a and 152a of the frames 142 and 152, respectively. In the second embodiment, the first magnets M1 are housed and fixed in respective magnet housings 161 and 162 formed in the rear walls 142a and 152a. The magnet housings 161 and 162 are erected outward from the rear walls 142a and 152a. The first magnet M1 is thus positioned at the end portion on the grip 6 side in the vibration applicator 5. The configuration, the fixing method, and the like of the first magnet M1 are similar as in the first embodiment. In the second embodiment, the first magnet M1 is shaped like a disk (or like a button).

In FIG. 23 illustrating the vibration applicator 5 as viewed from the grip 6, the first magnets M1 are fixed between the contact terminals T1a and T1a and between the contact terminals T1b and T1b, respectively. However, the arrangement relationship of the first magnets M1, the contact terminals T1a, T1a, and the contact terminals T1b, T1b is not limited to the manner shown in FIG. 23.

<Grip>

Figure 24:
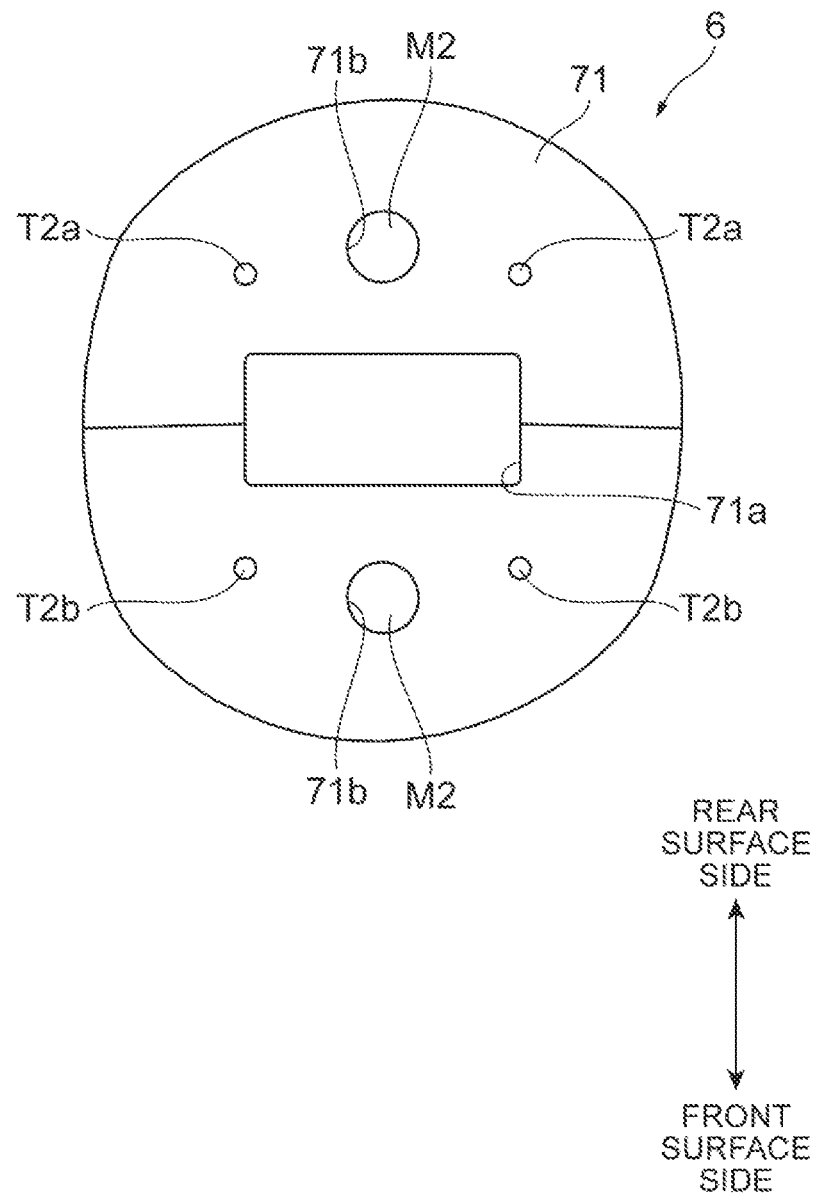
FIG. 24 is a diagram showing the grip of the toothbrush vibrator shown in FIG. 21 as viewed from the vibration applicator.

Referring to FIG. 21 and FIG. 24, the grip 6 of the vibrator 1A will be described. The grip 6 is a portion gripped by the user, similar to the grip 4, and is internally provided with the power supply unit 20 illustrated in FIG. 4. Also in the grip 6, the switch 22 and the vibration controller 23 in the power supply unit 20 and the LEDs 30a, 30b, and 30c are mounted on the circuit board 90 fixed to the case 70 of the grip 6. FIG. 21 then illustrates the manner, similar to the manner shown in FIG. 3, in which tubular portions 75, 76a, 76b, and 76c are provided on the inside of the peripheral wall 74 of the case 70. The grip 6 may have a nameplate film P.

As shown in FIG. 21, the grip 6 is similar to the grip 4, except that a secondary battery 21C is used as the power source 21 instead of the dry battery 21A and that the arrangement of the contact terminals T2a and T2b is changed in accordance with the arrangement of the contact terminals T1a and T1b in the vibration applicator 5. Focusing on these differences, the grip 6 will be described.

In the grip 6, the secondary battery 21C is fixed as the power source 21 on the partition plate 81. FIG. 21 does not illustrate wiring from the secondary battery 21C to the circuit board 90 fixed to the case 70, or the related terminals, as in the first embodiment. The case 70 of the grip 6 may include, for example, a charging terminal in the case 70 for charging the secondary battery 21C. Alternatively, the case rear wall 73 may be opened and closed or detachable from the body of the case 70 to connect a charging terminal to the secondary battery 21C.

Also in the grip 6, the contact terminals T2a and T2b are fixed to the case front wall 71. The contact terminal T2a is fixed to a position corresponding to the contact terminal T1a, and the contact terminal T2b is fixed to a position corresponding to the contact terminal T1b. Examples of the contact terminals T2a and T2b, the fixing state of the contact terminals T2a and T2b to the case front wall 71, and the like are similar as in the contact terminals T2a and T2b described in the first embodiment.

The second magnet M2 is fixed to a position corresponding to the first magnet M1 in the case front wall 71. In the second embodiment, the second magnet M2 is a ball-shaped permanent magnet and is housed and fixed in a depression 71b formed in the outer surface of the case front wall 71. In order to fix the second magnet M2 in the depression 71b in this way, the thickness of the case front wall 71 may be greater in the second embodiment than in the first embodiment.

Figure 25:
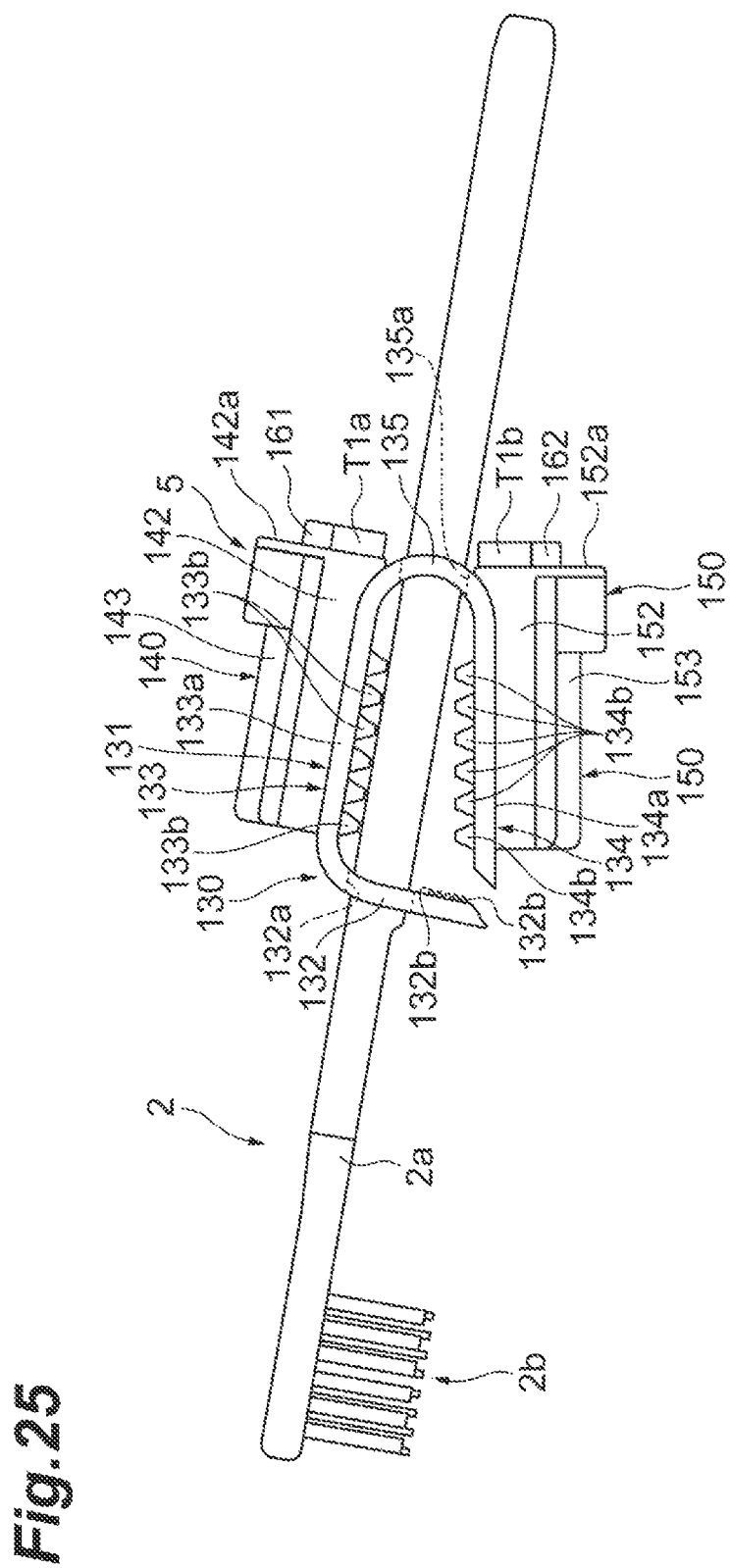
FIG. 25 is a diagram for explaining a method of attaching a toothbrush to the vibration applicator.

In use of the vibrator 1A, as shown in FIG. 25, first of all, the locked state between the stopper portion 132b and the front end of the second base plate 134a is released, and the handle 2a of the toothbrush 2 is inserted through the first opening 132a and the second opening 135a.

Figure 26:
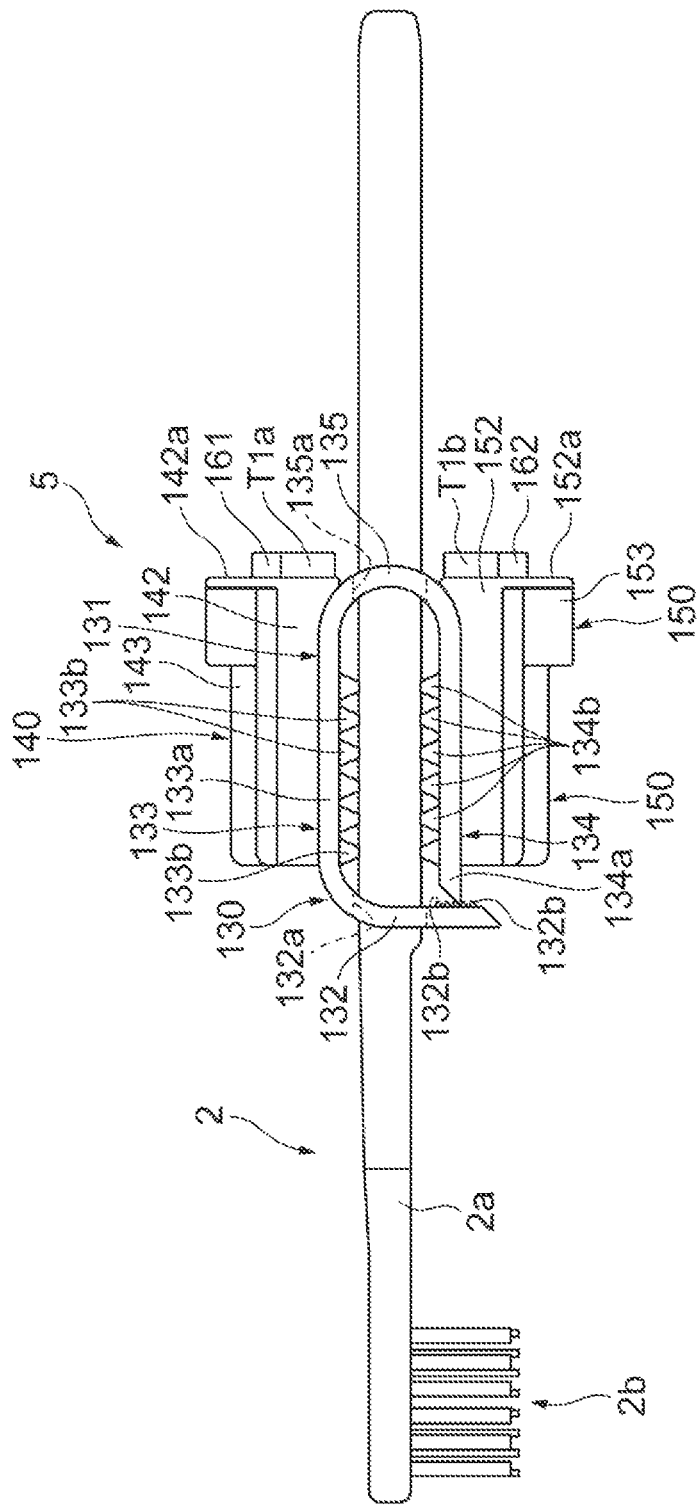
FIG. 26 is a diagram for explaining the step subsequent to the step shown in FIG. 25 in the method of attaching a toothbrush to the vibration applicator.

Next, as shown in FIG. 26, the distance between the first holding portion 133 and the second holding portion 134 is reduced. Reducing the distance between the first holding portion 133 and the second holding portion 134 in this way allows the first projections 133b and the second projections 134b to abut with the handle 2a, such that the handle 2a is held between the first holding portion 133 and the second holding portion 134. When the first projections 133b and the second projections 134b are formed of an elastic material such as rubber, the tip ends of the first projections 133b and the second projections 134b deform so as to conform to the shape of the handle 2a, thereby to ensure that the handle 2a is held between the first holding portion 133 and the second holding portion 134.

In the state in which the handle 2a is sandwiched between the first holding portion 133 and the second holding portion 134, the stopper portion 132b corresponding to the distance between the first holding portion 133 and the second holding portion 134 locks the front end of the second base plate 134a. This keeps the state of the handle 2a sandwiched between the first holding portion 133 and the second holding portion 134. That is, the toothbrush 2 is held by the vibration applicator 5.

Subsequently, the vibration applicator 5 is attached to the grip 6 using the magnetic force of the first magnets M1 and the second magnets M2. This enables the toothbrush 2 to be used as an electric toothbrush and allows the user to brush his/her teeth with the toothbrush 2 functioning as an electric toothbrush, in the same manner as in the first embodiment.

Also in the vibrator 1A described in the second embodiment, the vibration applicator 5 is detachably attached to the grip 6. The vibrator 1A therefore has at least similar operations and effects as the vibrator 1.

In the vibration applicator 5 of the vibrator 1A, a plurality of stopper portions 132b are formed at the end portion of the end plate 132 on the second base plate 134a side. With this configuration, the single vibration applicator 5 can be used to hold a plurality of toothbrushes 2 with different sizes in the vibration applicator 5 by locking the front end of the second base plate 134a with different stopper portions 132b. That is, the vibrator 1A can be used for toothbrushes 2 with different sizes.

In the vibration applicator 5, the first magnets M1 are fixed in the magnet housings 161 and 162 provided in the rear walls 142a and 152a of the frames 142 and 152. With this configuration, when the vibration applicator 5 is attached to the grip 6, as shown in FIG. 21, the vibration applicator 5 and the grip 6 are in contact with each other at the positions of the two first magnets M1. That is, the vibration applicator 5 and the grip 6 are in contact with each other substantially at two points. In this manner in which the vibration applicator 5 and the grip 6 are substantially in point contact, the vibration applicator 5 easily swings relative to the grip 6. In other words, the vibration of the vibration applicator 5 is less hindered by the grip 6. As a result, the vibration of the vibration applicator 5 can be transmitted to the toothbrush 2 with high intensity and efficiently.

As shown in FIG. 21, in the manner in which the ball-shaped second magnets M2 are used, the contact area between the first magnet M1 and the second magnet M2 can be reduced. Also in this respect, the point contact between the vibration applicator 5 and the grip 6 is implemented. Thus, as previously mentioned, the vibration of the vibration applicator 5 can be transmitted to the toothbrush 2 with high intensity and efficiently.

Although the embodiments of the present invention have been described above, the present invention is shown by the claims and is not limited to these examples, and it is intended that all equivalents to the claims and modifications within the scope of the claims are embraced herein.

(First Modification)

Figure 27:
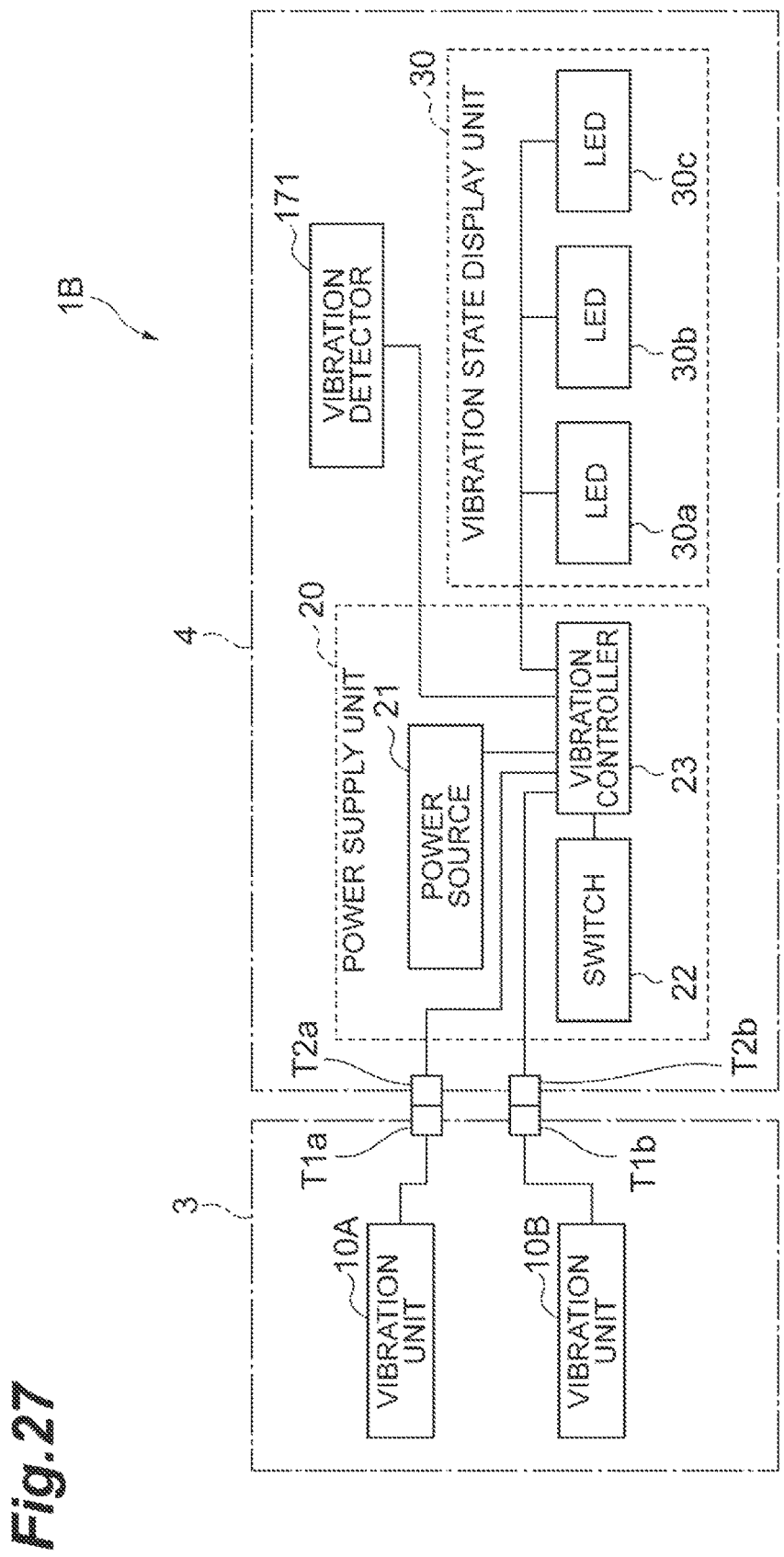
FIG. 27 is a diagram for explaining a toothbrush vibrator in a first modification.

Referring to FIG. 27, a vibrator (toothbrush vibrator) 1B will be described as a first modification to the vibrator 1. FIG. 27 is a block diagram of the vibrator 1B when the vibration applicator 3 is attached to the grip 4 and mainly illustrates the electrical connection relation.

As shown in FIG. 27, the vibrator 1B differs from the vibrator 1 in that the grip 4 includes a vibration detector 171. Except for this difference, the configuration of the vibrator 1B is similar to the vibrator 1, and the difference will be described.

The vibration detector 171 detects a vibration state of the vibrator 1B (more specifically, the grip 4) in use of the vibrator 1B (during toothbrushing). The vibration detector 171 is a vibration sensor, for example, as used in Verification Experiments 1 to 4. The vibration detector 171 may be fixed, for example, on the inner wall of the case 70.

The vibration detector 171 is electrically connected to the vibration controller 23 in the power supply unit 20 and transmits the detection result to the vibration controller 23. The vibration controller 23 controls the vibration state of the vibration units 10A and 10B in accordance with the detection result from the vibration detector 171. Also in the first modification, the vibration controller 23 may individually control each of the vibration unit 10A and the vibration unit 10B.

In the vibrator 1B configured as described above, the vibration state of the vibration applicator 3 can be performed by a feed-back control. This configuration further ensures that, for example, any desired vibration states such as the low vibration state, the middle vibration state, and the high vibration state are kept.

In addition, for example, if a memory is mounted on the circuit board 90 and the vibration state preferred by the user is stored in the memory, so that feed-back control can be performed in accordance with the preferred vibration state. In this case, the vibrator 1B may have a mechanism for storage in the memory.

Although the example in which the vibration detector 171 is built into the grip 4 has been described in the first modification, the vibration detector 171 may be fixed in the inside of the vibration applicator 3. In any configuration, the user can brush his/her teeth with the vibration state kept within a predetermine range even when applying the toothbrush 2 on the teeth (even when the load varies so as to suppress vibration). In the manner in which the vibration detector 171 is built into the vibration applicator 3, the vibration detector 171 may be configured to transmit its detection result to the vibration controller 23 by wire or by radio.

(Second Modification)

Figure 28:
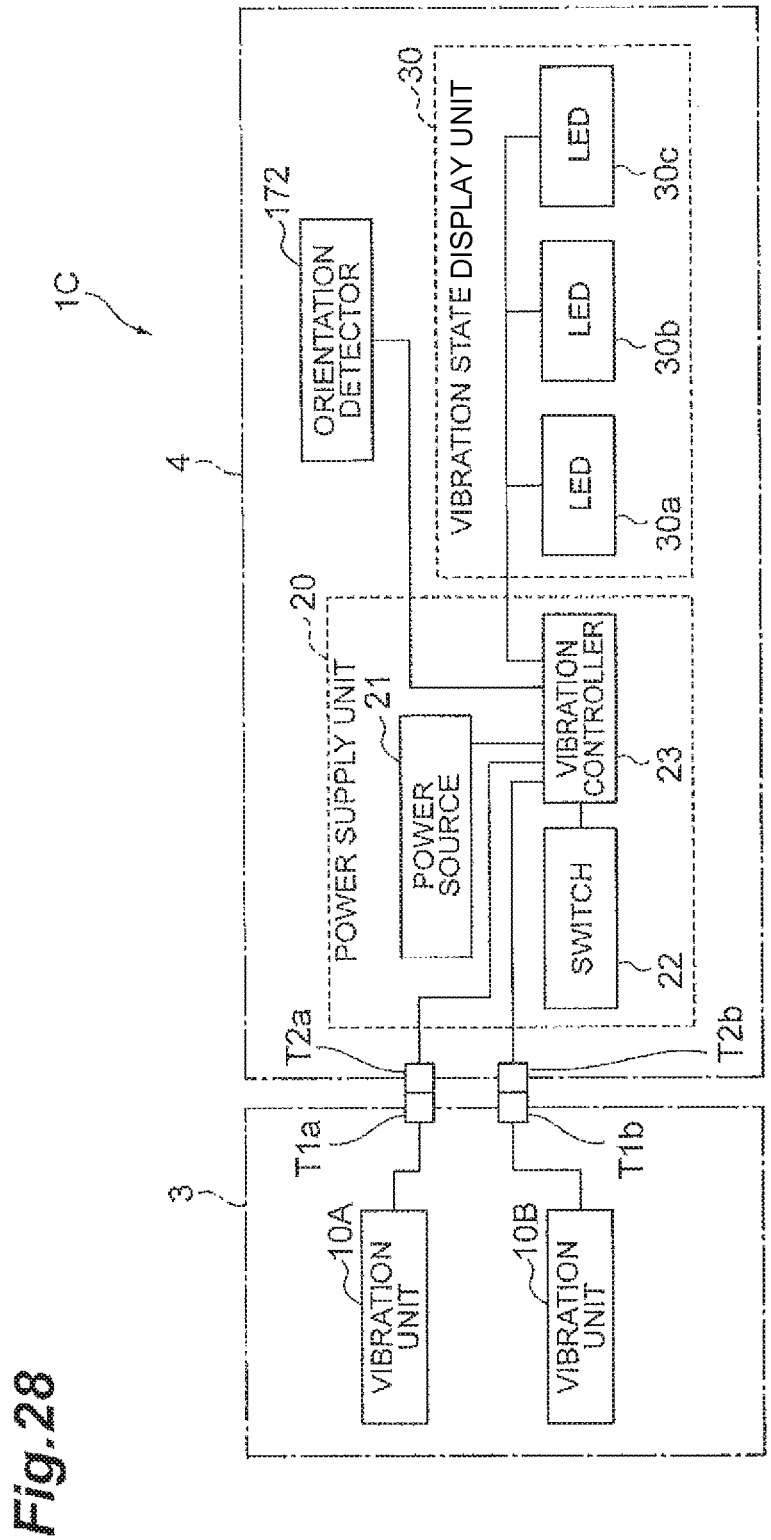
FIG. 28 is a diagram for explaining a toothbrush vibrator in a second modification.

Referring to FIG. 28, a vibrator 1C will be described as a second modification to the vibrator 1. FIG. 28 is a block diagram of the vibrator 1C when the vibration applicator 3 is attached to the grip 4 and mainly illustrates the electrical connection relation.

As shown in FIG. 28, the vibrator 1C differs from the vibrator 1 in that the grip 4 includes an orientation detector 172. Except for this difference, the vibrator 1C has a similar configuration as the vibrator 1, and the difference will be described.

The orientation detector 172 detects an orientation of the grip 4. The orientation detector 172 is electrically connected to the vibration controller 23 in the power supply unit 20 and transmits the detection result to the vibration controller 23. The orientation detector 172 is, for example, a gyro sensor. The orientation detector 172 may be fixed on the inner wall of the case 70.

As shown in FIG. 28, in the manner in which the grip 4 includes the orientation detector 172, the vibration controller 23 accepts a detection result from the orientation detector 172 and then controls the vibration state in accordance with the orientation of the grip 4 corresponding to the detection result. Also in the second modification, the vibration controller 23 may individually control each of the vibration unit 10A and the vibration unit 10B.

Since the toothbrush 2 is held in the vibrator 1C, the orientation of the grip 4 corresponds to the orientation of the toothbrush 2. Thus, the detection of the orientation of the grip 4 corresponds to the detection of the orientation of the toothbrush 2.

During toothbrushing, the user changes the orientation of the toothbrush 2 depending on a section of the teeth to be brushed and applies the bristles 2b on the desired position. For example, when the bristles 2b come into contact with a soft portion such as gum, the vibration of the vibration units 10A and 10B is controlled in the low vibration state so as not to damage the gum, whereas when a hard portion such as tooth enamel is to be brushed, the vibration is controlled in a high vibration state. With such a configuration of the vibrator 1C, the state of vibration transmitted to the toothbrush 2 can be controlled depending on a section that the bristles 2b is applied to.

The first and second modifications may be combined with each other. Furthermore, the first and second modifications are applicable to the vibrator 1A. That is, the vibrator 1A may further include at least one of the vibration detector 171 and the orientation detector 172.

In the toothbrush vibrator, as long as the vibration applicator and the grip are configured to be attachable to and detachable from each other, the method of attaching and detaching them is not limited to the manner using magnetic force of magnets. Although eccentric weighted motors that are vibration motors have been illustrated as the vibration units 10A and 10B, any configuration that can generate vibration may be used.

The grip may be configured such that the rear side of the handle of the toothbrush can be fixed on the inside of the grip. Fixing the rear side of the handle of the toothbrush in this manner facilitates vibration of the toothbrush 2 on the bristles 2b side (front side).

The power supply or the vibration controller in the power supply may be built into the vibration applicator, for example.

The invention claimed is:

1. A toothbrush vibrator comprising:
a vibration applicator having a case that allows a toothbrush to pass therethrough and holds the toothbrush and applying vibration to the toothbrush, the case being hollow pillar-shaped body; and
a grip detachably connected to the vibration applicator and gripped by a user,
wherein the grip has a case that is a hollow pillar-shaped body and is capable of housing a portion of a handle of the toothbrush that protrudes from the vibration applicator toward the grip,
the vibration applicator includes a first magnet provided at a grip-side end portion of the vibration applicator,
the grip includes a second magnet provided at a vibration applicator-side end portion of the grip, and
the vibration applicator and the grip are detachably connected by force of the first magnet and the second magnet attracting each other.

2. The toothbrush vibrator according to claim 1, wherein in a state in which the vibration applicator and the grip are connected to each other, the vibration applicator and the grip are in point contact.

3. The toothbrush vibrator according to claim 1, wherein the vibration applicator includes a vibration unit generating vibration to be applied to the toothbrush,
the grip includes a power supply unit supplying the vibration unit with electric power, and
the power supply unit is electrically connected to the vibration unit in a state in which the grip is connected to the vibration applicator.

4. The toothbrush vibrator according to claim 3, wherein a first terminal portion electrically connected to the vibration unit is provided at a grip-side end portion of the vibration applicator,
a second terminal portion electrically connected to the power supply unit is provided at a vibration applicator-side end portion of the grip, and
the first terminal portion and the second terminal portion are electrically in contact with each other in a state in which the vibration applicator and the grip are connected to each other.

5. The toothbrush vibrator according to claim 3, wherein one of the vibration applicator and the grip includes a vibration detector, and
the power supply unit controls a vibration state of the vibration unit in accordance with a detection result from the vibration detector.

6. The toothbrush vibrator according to claim 3, wherein the grip includes an orientation detector, and
the power supply unit controls a vibration state of the vibration unit in accordance with a detection result from the orientation detector.

7. The toothbrush vibrator according to claim 3, wherein the vibration unit is an eccentric weighted motor.

* * * * *